US012116387B2

(12) United States Patent
Der Torossian Torres et al.

(10) Patent No.: US 12,116,387 B2
(45) Date of Patent: Oct. 15, 2024

(54) ANTIMICROBIAL PEPTIDES

(71) Applicant: The Trustees of the University of Pennsylvania, Philadelphia, PA (US)

(72) Inventors: Marcelo Der Torossian Torres, Philadelphia, PA (US); Cesar de la Fuente-Nunez, Philadelphia, PA (US); Gislaine G. O. Silva, Campo Grande MS (BR); Octavio L Franco, Campo Grande (BR)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 72 days.

(21) Appl. No.: 17/932,077

(22) Filed: Sep. 14, 2022

(65) Prior Publication Data
US 2023/0086360 A1 Mar. 23, 2023

Related U.S. Application Data

(60) Provisional application No. 63/243,845, filed on Sep. 14, 2021.

(51) Int. Cl.
| | |
|---|---|
| C07K 14/435 | (2006.01) |
| A01N 63/50 | (2020.01) |
| A61K 38/00 | (2006.01) |
| A61P 31/04 | (2006.01) |
| C07K 1/107 | (2006.01) |
| C07K 7/06 | (2006.01) |

(52) U.S. Cl.
CPC ........ *C07K 14/43568* (2013.01); *A01N 63/50* (2020.01); *A61P 31/04* (2018.01); *C07K 1/1075* (2013.01); *C07K 7/06* (2013.01); *A61K 38/00* (2013.01); *C07K 2319/00* (2013.01)

(58) Field of Classification Search
CPC .. C07K 14/43568; C07K 1/1075; C07K 7/06; C07K 2319/00; C07K 7/08; A01N 63/50; A01N 37/46; A61P 31/04; A61K 38/00; A01P 1/00
See application file for complete search history.

(56) References Cited

U.S. PATENT DOCUMENTS

| | | | |
|---|---|---|---|
| 5,519,115 A * | 5/1996 | Mapelli | A01N 63/50 530/324 |
| 2021/0347823 A1* | 11/2021 | Lu | A61P 31/10 |
| 2022/0064219 A1* | 3/2022 | de la Fuente-Nunez | A61K 38/00 |

FOREIGN PATENT DOCUMENTS

BR 102015028254-0 A2 * 5/2017 ............. C07K 7/08

OTHER PUBLICATIONS

Lima et al. Synthetic antimicrobial peptides: Characteristics, design, and potential as alternative molecules to overcome microbial resistance. Life Sciences. vol. 278, Aug. 1, 2021, accessible online May 24, 2021, pp. 1-11. (Year: 2021).*
Tisch-Idelson et al. Structure-function relationship in the interaction of mastoparan analogs with neutrophil NADPH oxidase. Biochemical Pharmacology 61 (2001) pp. 1063-1071. (Year: 2001).*
Zhou et al., "Clinical course and risk factors for mortality of adult inpatients with COVID-19 in Wuhan, China: a retrospective cohort study", Lancet, 2020, vol. 395, No. 10229, pp. 1054-1062.
Barany-Wallje E. et al., "Differential membrane perturbation caused by the cell penetrating peptide Tp10 depending on attached cargo", FEBS Lett, May 2007, vol. 581, No. 13, pp. 2389-2393.
Boase et al., "Polynitroxide copolymers to reduce biofilm fouling on surfaces", Polym Chem., 2018, vol. 9, pp. 5308-5318.
Brouwer et al., "The Pharmacology of Radiolabeled Cationic Antimicrobial Peptides", JPharm Sci, 2008, vol. 97, No. 5, pp. 1633-1651.
Candido et al., "Short Cationic Peptide Derived from Archaea with Dual Antibacterial Properties and Anti-Infective Potential", ACS Infect Dis., 2019, vol. 5, No. 7, pp. 1081-1086.
Cardoso et al., "A Computationally Designed Peptide Derived from Escherichia coli as a Potential Drug Template for Antibacterial and Antibiofilm Therapies", ACS Infect Dis. 2018, vol. 4, No. 12, pp. 1727-1736.
Centers for Disease Control and Prevention, 2019 Antimicrobial Resistant Threats Report Available at: https://www.cdc.gov/drugresistance/biggest-threats.html.
Chen et al., "Determination of the helix and beta form of proteins in aqueous solution by circular dichroism", Biochemistry, Jul. 1974, vol. 13, No. 16, pp. 3350-3359.
Chen X, et al., "Evaluation of the bioactivity of a mastoparan peptide from wasp venom and of its analogues designed through targeted engineering", Int J Biol Sci., 2018, vol. 14, No. 6, pp. 599-607.
Conlon et al., "Peptides with potent cytolytic activity from the skin secretions of the North American leopard frogs, Lithobates blairi and Lithobates yavapaiensis", Toxicon, 2009, vol. 53, No. 7-8, pp. 699-705.

(Continued)

*Primary Examiner* — Marcela M Cordero Garcia
(74) *Attorney, Agent, or Firm* — BakerHostetler

(57) ABSTRACT

Provided herein are synthetic peptides with enhanced antimicrobial and antibiofilm characteristics, and are biocompatible with mammalian cellular systems. The disclosed synthetic antimicrobial moieties include a mastoparan peptide having SEQ ID NO:1 and a pentapeptide motif formed from phenylalanine, leucine, proline, and two isoleucine residues, wherein the pentapeptide motif is conjugated the N-terminus of the mastoparan peptide. Also provided are compositions comprising the synthetic peptides, as well as methods of treating a microbial infection or removing a biofilm using the peptides.

22 Claims, 9 Drawing Sheets
(9 of 9 Drawing Sheet(s) Filed in Color)
Specification includes a Sequence Listing.

(56) References Cited

OTHER PUBLICATIONS

Delaglio F, et al., "NMRPipe: a multidimensional spectral processing system based on UNIX pipes", JBiomol NMR, 1995, vol. 6, No. 3, pp. 277-293.
Fuente-Nunez et al., "Bacterial biofilm development as a multicellular adaptation: antibiotic resistance and new therapeutic strategies", Curr Opin Microbiol., Oct. 2013, vol. 16, No. 5, pp. 580-589.
Fuente-Nunez et al., "Next-generation precision antimicrobials: towards personalized treatment of infectious diseases", Curr Opin Microbiol, 2017, vol. 37, pp. 95-102.
Goraya J, et al. "Peptides with antimicrobial activity from four different families isolated from the skins of the North American frogs Rana luteiventris, Rana berlandieri and Rana pipiens", Eur J Biochem, 2000, vol. 267, No. 3, pp. 894-900.
Greenfield NJ, "Using circular dichroism spectra to estimate protein secondary structure", Nature Protocols, 2006, vol. 1, No. 6, pp. 2876-2890.
Hernandez-Gras et al., "A hydrophobic proline-rich motif is involved in the intracellular targeting of temperature-induced lipocalin", 2015, Plant Mol Biol., vol. 88, No. 3, pp. 301-311.
Higashijima et al., "Mastoparan, a peptide toxin from wasp venom, mimics receptors by activating GTP-binding regulatory proteins (G proteins)", J Biol Chem, 1988, vol. 263, No. 14, pp. 6491-6494.
Higashijima et al., "Regulation of Gi and Go by mastoparan, related amphiphilic peptides, and hydrophobic amines. Mechanism and structural determinants of activity", J Biol Chem, 1990, vol. 265, No. 24, pp. 14176-14186.
Hyberts et al., "The solution structure of eglin c based on measurements of many NOEs and coupling constants and its comparison with X-ray structures", Protein Sci, 1992, vol. 1, No. 6, pp. 736-751.
Irazazabal LN, et al., "Selective amino acid substitution reduces cytotoxicity of the antimicrobial peptide mastoparan", Biochim Biophys Acta, 2016, vol. 1858, No. 11, pp. 2699-2708.
Johnson et al., "NMR View: A computer program for the visualization and analysis of NMR data", Journal of Biomolecular NMR, 1994, vol. 4, No. 5, pp. 603-614.
Kim et al., "Evaluation of the Immunomodulatory Activity of the Chicken NK-Lysin-Derived Peptide cNK-2", Sci Rep, 2017, vol. 7, 45099, pp. 11.
Koradi R. et al., "MOLMOL: a program for display and analysis of macromolecular structures", J Mol Graph, 1996, vol. 14, No. 1, pp. 51-55.
Lazar et al., "Antibiotic-resistant bacteria show widespread collateral sensitivity to antimicrobial peptides", Nat Microbiology, 2018, vol. 3, No. 6, pp. 718-731.
Lewis et al., "Therapeutic potential of venom peptides", Nature Reviews Drug Discovery, 2003, vol. 2, No. 10, pp. 790-802.
Lima et al., "Antimicrobial and immunomodulatory activity of host defense peptides, clavanins and LL-37, in vitro : An endodontic perspective", Peptides, 2017, vol. 95, pp. 16-24.
Moreno SE, et al., "IL-12, but Not IL-18, Is Critical to Neutrophil Activation and Resistance to Polymicrobial Sepsis Induced by Cecal Ligation and Puncture", J Immunol vol. 177, No. 5, pp. 3218-3224.
Morens et al., "Predominant Role of Bacterial Pneumonia as a Cause of Death in Pandemic Influenza: Implications for Pandemic Influenza Preparedness", J Infect Dis, 2008, vol. 198, No. 7, pp. 962-970.
Mousli et al., "Activation of rat peritoneal mast cells by substance p. and mastoparan", J Pharmacol Exp Ther, 1989, vol. 250, No. 1, pp. 329-335.
Navon-Venezia S. et al., "Antibacterial Properties of Dermaseptin S4 Derivatives with In Vivo Activity", Antimicrob Agents Chemother, Mar. 2002 vol. 46, No. 3, pp. 689-694.
Nijnik et al., "Host defence peptides: antimicrobial and immunomodulatory activity and potential applications for tackling antibiotic-resistant infections", Emerg Health Threats J, 2009, 2: e1, pp. 7.
Oshiro et al., "Computer-Aided Design of Mastoparan-like Peptides Enables the Generation of Nontoxic Variants with Extended Antibacterial Properties", J Med Chem, 2019, vol. 62, No. 17, pp. 8140-8151.
Pane K, et al., "Identification of Novel Cryptic Multifunctional Antimicrobial Peptides from the Human Stomach Enabled by a Computational-Experimental Platform", ACS Synth Biol, 2018, vol. 7, No. 9, pp. 2105-2115.
Pizzo E, et al., "Novel bioactive peptides from PD-L1/2, a type 1 ribosome inactivating protein from *Phytolacca dioica* L. Evaluation of their antimicrobial properties and anti-biofilm activities", Biochimica et Biophysica Acta (BBA)—Biomembranes, 2018, vol. 1860, No. 7, pp. 1425-1435.
Pletzer D. et al., "New Mouse Model for Chronic Infections by Gram-Negative Bacteria Enabling the Study of Anti Infective Efficacy and Host-Microbe Interactions", MBio, 2017, vol. 8, No. 1, e00140-17.
Porto et al., "In silico optimization of a guava antimicrobial peptide enables combinatorial exploration for peptide design", Nat Commun, 2018, vol. 9, No. 1, 1490, 12 Pages.
Ray A. et al., "Isolation of Mouse Peritoneal Cavity Cells", J Vis Exp, 2010, vol. 35, pp. 3.
Rudd et al., "Global, regional, and national sepsis incidence and mortality, 1990-2017: analysis for the Global Burden of Disease Study", Lancet, 2020, vol. 395, No. 10219, pp. 200-211.
Schwieters et al., "The Xplor-NIH NMR molecular structure determination package", J Magn Reson, 2003, vol. 160, No. 1, pp. 65-73.
Shen et al., "TALOS+: a hybrid method for predicting protein backbone torsion angles from NMR chemical shifts", J Biomol NMR, vol. 44, No. 4, pp. 213-223.
Silva et al., "An anti-infective synthetic peptide with dual antimicrobial and immunomodulatory activities", Sci Rep, 2016, vol. 6, No. 1, 35465.
Souza et al., "Structure-activity relationship of mastoparan analogs: Effects of the number and positioning of Lys residues on secondary structure, interaction with membrane-mimetic systems and biological activity", Peptides, 2015, vol. 72, pp. 164-174.
Sreerama et al., "Estimation of protein secondary structure from circular dichroism spectra: Comparison of CONTIN, SELCON, and CDSSTR methods with an expanded reference set", Anal Biochem, vol. 287, No. 2, pp. 252-260.
Sreerama et al., "On the analysis of membrane protein circular dichroism spectra", Protein Sci, 2004, vol. 13, No. 1, pp. 100-112.
Torres et al., "Decoralin Analogs with Increased Resistance to Degradation and Lower Hemolytic Activity", Chemistry Select, 2017, vol. 2, No. 1, pp. 18-23.
Torres et al., "Peptide Design Principles for Antimicrobial Applications", J Mol Biol. in Press, 2019.
Torres et al., "Structure-function-guided exploration of the antimicrobial peptide polybia-CP identifies activity determinants and generates synthetic therapeutic candidates", Commun Biol, 2018, 1, 221.
Vert M, et al., "Terminology for biorelated polymers and applications (IUPAC Recommendations 2012)", Pure Appl Chem, 2012, vol. 84, No. 2, pp. 377-410.
Wang et al., "APD3: the antimicrobial peptide database as a tool for research and education", Nucleic Acids Res, 2016, vol. 44, (D1), pp. D1087-D1093.
Wiederstein et al., "ProSA-web: interactive web service for the recognition of errors in three-dimensional structures of proteins", Nucleic Acids Res, 2007, vol. 35, pp. 407-410.
Yang et al., "Antimicrobial peptides from the venom gland of the social wasp Vespa tropica", Toxicon, 2013, vol. 74, pp. 151-157.

* cited by examiner

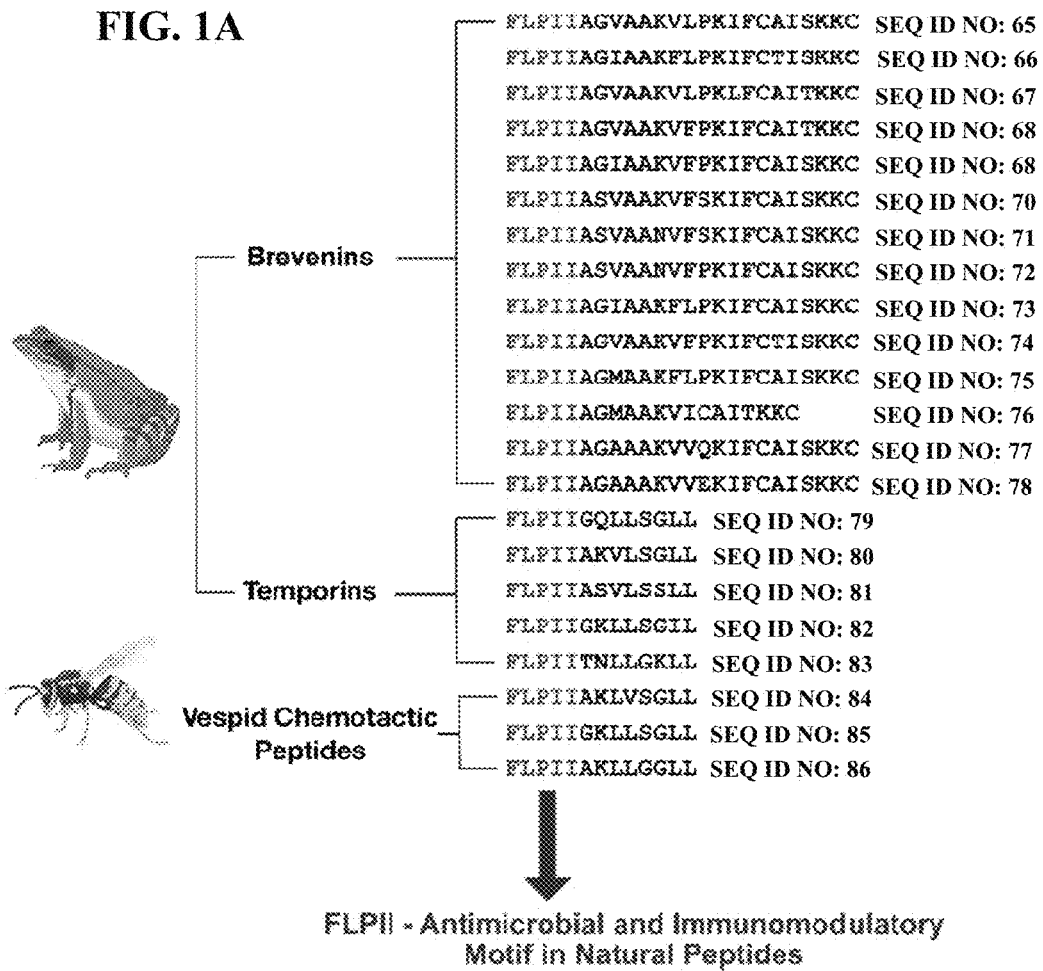

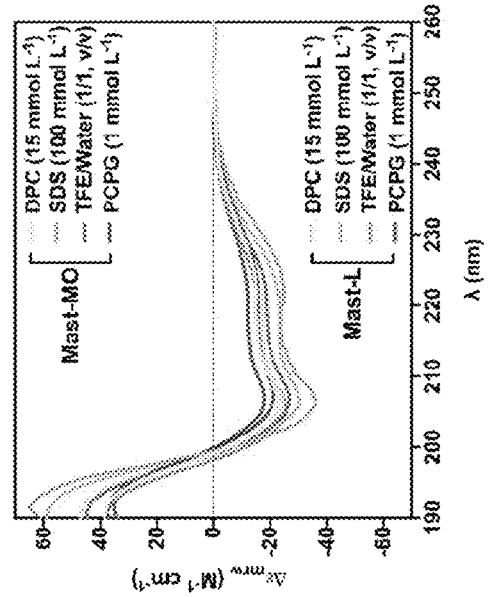
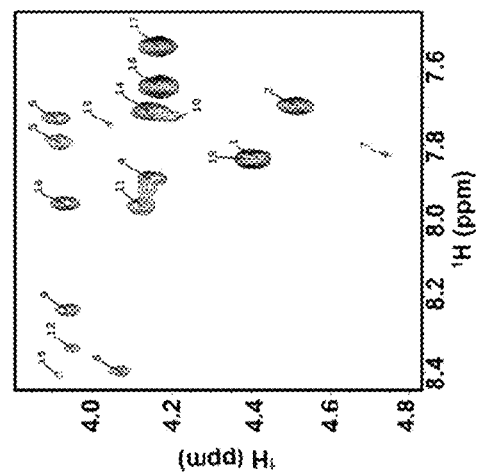
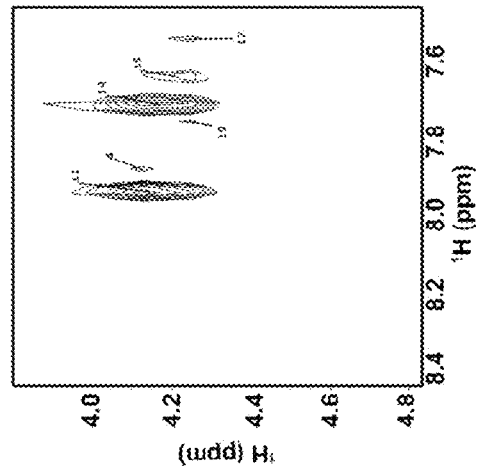
FIG. 2C
FIG. 2B
FIG. 2A

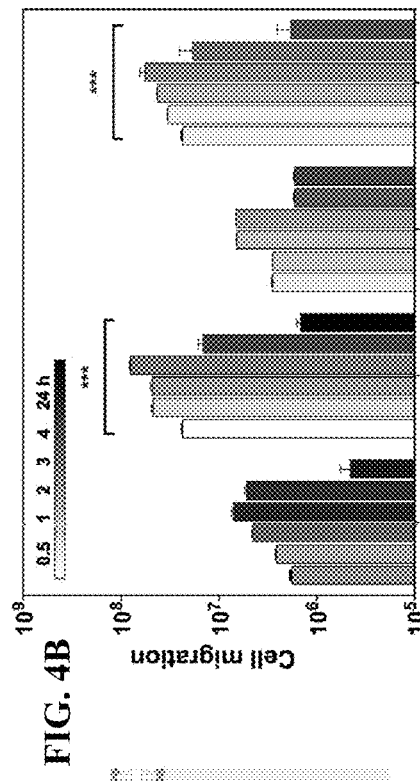
FIG. 4A
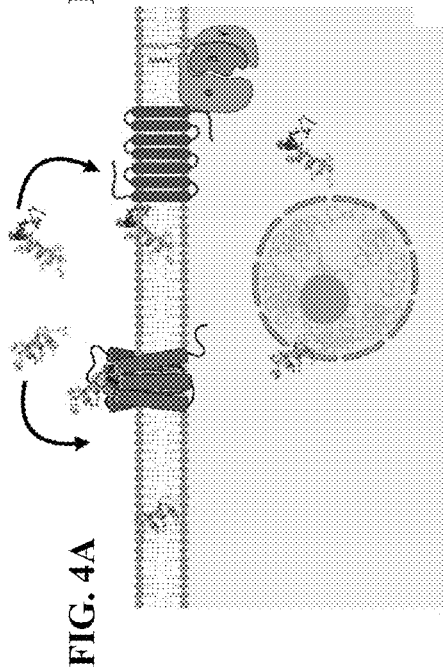
FIG. 4B
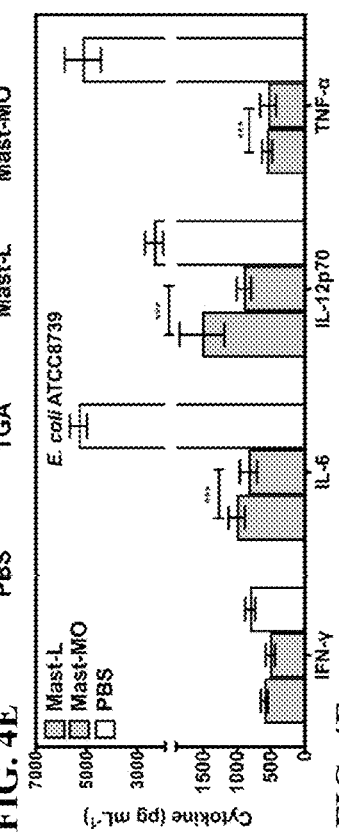
FIG. 4C
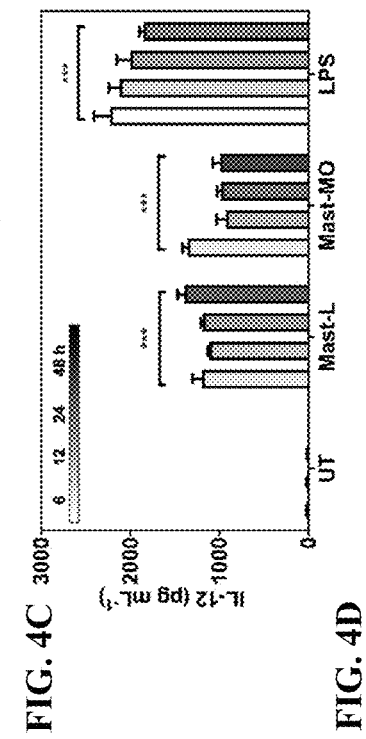
FIG. 4D
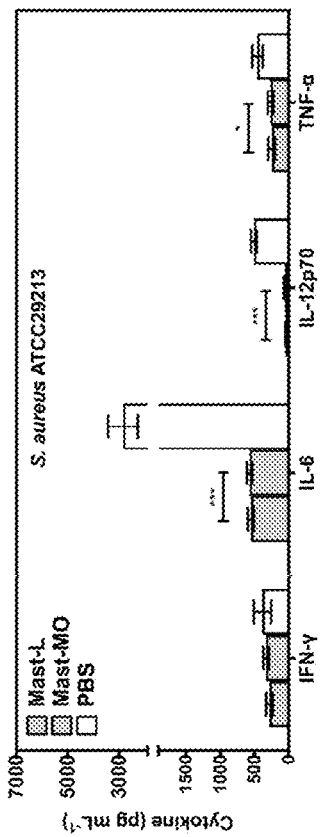
FIG. 4E
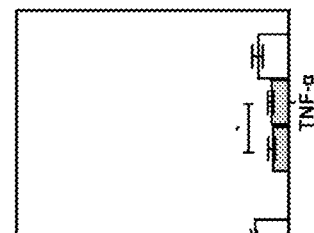
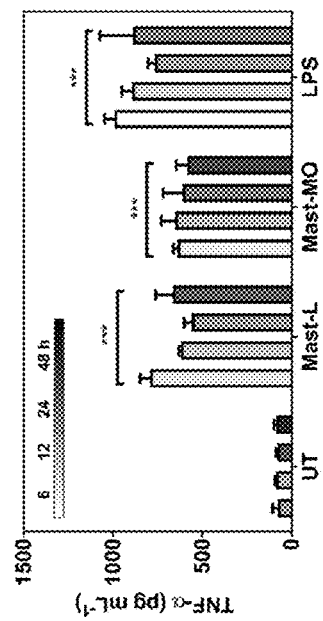
FIG. 4F S. aureus ATCC33591
(MRSA) Untreated S. aureus ATCC33591
(MRSA) Mast-L (4 µg/mL)

S. aureus ATCC33591
(MRSA) Mast-MO (4 µg/mL)

E. coli ATCC0157
Untreated

E. coli ATCC0157
Mast-L (4 µg/mL)

E. coli ATCC0157
Mast-MO (4 µg/mL)

```
SEQUENCE LISTING

Sequence total quantity: 86
SEQ ID NO: 1             moltype = AA  length = 13
FEATURE                  Location/Qualifiers
REGION                   1..13
                         note = misc_feature - amino acid sequence of mast-L
source                   1..13
                         mol_type = protein
                         organism = Vespula lewisii
SEQUENCE: 1
NLKALAALAK KIL                                                          13

SEQ ID NO: 2             moltype = AA  length = 27
FEATURE                  Location/Qualifiers
REGION                   1..27
                         note = Synthetic: Galparan
source                   1..27
                         mol_type = protein
                         organism = synthetic construct
SEQUENCE: 2
GWTLNSAGYL LGPINLKALA ALAKKIL                                           27

SEQ ID NO: 3             moltype = AA  length = 27
FEATURE                  Location/Qualifiers
REGION                   1..27
                         note = Synthetic: Transportan
source                   1..27
                         mol_type = protein
                         organism = synthetic construct
SEQUENCE: 3
GWTLNSAGYL LGKINLKALA ALAKKIL                                           27

SEQ ID NO: 4             moltype = AA  length = 21
FEATURE                  Location/Qualifiers
REGION                   1..21
                         note = Synthetic: TP10
source                   1..21
                         mol_type = protein
                         organism = synthetic construct
SEQUENCE: 4
AGYLLGKINL KALAALAKKI L                                                 21

SEQ ID NO: 5             moltype = AA  length = 19
FEATURE                  Location/Qualifiers
REGION                   1..19
                         note = Synthetic: Mast-MO
source                   1..19
                         mol_type = protein
                         organism = synthetic construct
SEQUENCE: 5
FLPIIINLKA LAALAKKIL                                                    19
```

```
SEQ ID NO: 6           moltype = AA   length = 19
FEATURE                Location/Qualifiers
REGION                 1..19
                       note = Synthetic
source                 1..19
                       mol_type = protein
                       organism = synthetic construct
SEQUENCE: 6
LFIIPINLKA LAALAKKIL                                            19

SEQ ID NO: 7           moltype = AA   length = 19
FEATURE                Location/Qualifiers
REGION                 1..19
                       note = Synthetic
source                 1..19
                       mol_type = protein
                       organism = synthetic construct
SEQUENCE: 7
IFLPIINLKA LAALAKKIL                                            19

SEQ ID NO: 8           moltype = AA   length = 19
FEATURE                Location/Qualifiers
REGION                 1..19
                       note = Synthetic
source                 1..19
                       mol_type = protein
                       organism = synthetic construct
SEQUENCE: 8
IIPFLINLKA LAALAKKIL                                            19

SEQ ID NO: 9           moltype = AA   length = 19
FEATURE                Location/Qualifiers
REGION                 1..19
                       note = Synthetic
source                 1..19
                       mol_type = protein
                       organism = synthetic construct
SEQUENCE: 9
LIPFIINLKA LAALAKKIL                                            19

SEQ ID NO: 10          moltype = AA   length = 19
FEATURE                Location/Qualifiers
REGION                 1..19
                       note = Synthetic
source                 1..19
                       mol_type = protein
                       organism = synthetic construct
SEQUENCE: 10
LIPIFINLKA LAALAKKIL                                            19

SEQ ID NO: 11          moltype = AA   length = 19
FEATURE                Location/Qualifiers
REGION                 1..19
                       note = Synthetic
source                 1..19
                       mol_type = protein
                       organism = synthetic construct
SEQUENCE: 11
LPIIFINLKA LAALAKKIL                                            19

SEQ ID NO: 12          moltype = AA   length = 19
FEATURE                Location/Qualifiers
REGION                 1..19
                       note = Synthetic
source                 1..19
                       mol_type = protein
                       organism = synthetic construct
SEQUENCE: 12
IIPLFINLKA LAALAKKIL                                            19

SEQ ID NO: 13          moltype = AA   length = 19
FEATURE                Location/Qualifiers
REGION                 1..19
                       note = Synthetic
source                 1..19
                       mol_type = protein
                       organism = synthetic construct
SEQUENCE: 13
ILIFPINLKA LAALAKKIL                                            19
```

```
SEQ ID NO: 14           moltype = AA   length = 19
FEATURE                 Location/Qualifiers
REGION                  1..19
                        note = Synthetic
source                  1..19
                        mol_type = protein
                        organism = synthetic construct
SEQUENCE: 14
PLIFIINLKA LAALAKKIL                                                  19

SEQ ID NO: 15           moltype = AA   length = 19
FEATURE                 Location/Qualifiers
REGION                  1..19
                        note = Synthetic
source                  1..19
                        mol_type = protein
                        organism = synthetic construct
SEQUENCE: 15
PLIIFINLKA LAALAKKIL                                                  19

SEQ ID NO: 16           moltype = AA   length = 19
FEATURE                 Location/Qualifiers
REGION                  1..19
                        note = Synthetic
source                  1..19
                        mol_type = protein
                        organism = synthetic construct
SEQUENCE: 16
PILFIINLKA LAALAKKIL                                                  19

SEQ ID NO: 17           moltype = AA   length = 19
FEATURE                 Location/Qualifiers
REGION                  1..19
                        note = Synthetic
source                  1..19
                        mol_type = protein
                        organism = synthetic construct
SEQUENCE: 17
IPFILINLKA LAALAKKIL                                                  19

SEQ ID NO: 18           moltype = AA   length = 19
FEATURE                 Location/Qualifiers
REGION                  1..19
                        note = Synthetic
source                  1..19
                        mol_type = protein
                        organism = synthetic construct
SEQUENCE: 18
IPLFIINLKA LAALAKKIL                                                  19

SEQ ID NO: 19           moltype = AA   length = 19
FEATURE                 Location/Qualifiers
REGION                  1..19
                        note = Synthetic
source                  1..19
                        mol_type = protein
                        organism = synthetic construct
SEQUENCE: 19
LFIIPINLKA LAALAKKIL                                                  19

SEQ ID NO: 20           moltype = AA   length = 19
FEATURE                 Location/Qualifiers
REGION                  1..19
                        note = Synthetic
source                  1..19
                        mol_type = protein
                        organism = synthetic construct
SEQUENCE: 20
IFLPIINLKA LAALAKKIL                                                  19

SEQ ID NO: 21           moltype = AA   length = 19
FEATURE                 Location/Qualifiers
REGION                  1..19
                        note = Synthetic
source                  1..19
                        mol_type = protein
                        organism = synthetic construct
SEQUENCE: 21
```

```
IIPFLINLKA LAALAKKIL                                                    19

SEQ ID NO: 22           moltype = AA   length = 19
FEATURE                 Location/Qualifiers
REGION                  1..19
                        note = Synthetic
source                  1..19
                        mol_type = protein
                        organism = synthetic construct
SEQUENCE: 22
LIPFIINLKA LAALAKKIL                                                    19

SEQ ID NO: 23           moltype = AA   length = 19
FEATURE                 Location/Qualifiers
REGION                  1..19
                        note = Synthetic
source                  1..19
                        mol_type = protein
                        organism = synthetic construct
SEQUENCE: 23
ILFIPINLKA LAALAKKIL                                                    19

SEQ ID NO: 24           moltype = AA   length = 19
FEATURE                 Location/Qualifiers
REGION                  1..19
                        note = Synthetic
source                  1..19
                        mol_type = protein
                        organism = synthetic construct
SEQUENCE: 24
IFLIPINLKA LAALAKKIL                                                    19

SEQ ID NO: 25           moltype = AA   length = 19
FEATURE                 Location/Qualifiers
REGION                  1..19
                        note = Synthetic
source                  1..19
                        mol_type = protein
                        organism = synthetic construct
SEQUENCE: 25
LIFIPINLKA LAALAKKIL                                                    19

SEQ ID NO: 26           moltype = AA   length = 19
FEATURE                 Location/Qualifiers
REGION                  1..19
                        note = Synthetic
source                  1..19
                        mol_type = protein
                        organism = synthetic construct
SEQUENCE: 26
ILFPIINLKA LAALAKKIL                                                    19

SEQ ID NO: 27           moltype = AA   length = 19
FEATURE                 Location/Qualifiers
REGION                  1..19
                        note = Synthetic
source                  1..19
                        mol_type = protein
                        organism = synthetic construct
SEQUENCE: 27
PFLIIINLKA LAALAKKIL                                                    19

SEQ ID NO: 28           moltype = AA   length = 19
FEATURE                 Location/Qualifiers
REGION                  1..19
                        note = Synthetic
source                  1..19
                        mol_type = protein
                        organism = synthetic construct
SEQUENCE: 28
FILIPINLKA LAALAKKIL                                                    19

SEQ ID NO: 29           moltype = AA   length = 19
FEATURE                 Location/Qualifiers
REGION                  1..19
                        note = Synthetic
source                  1..19
                        mol_type = protein
                        organism = synthetic construct
```

```
SEQUENCE: 29
IPPLIINLKA LAALAKKIL                                                    19

SEQ ID NO: 30          moltype = AA   length = 19
FEATURE                Location/Qualifiers
REGION                 1..19
                       note = Synthetic
source                 1..19
                       mol_type = protein
                       organism = synthetic construct
SEQUENCE: 30
LIIPFINLKA LAALAKKIL                                                    19

SEQ ID NO: 31          moltype = AA   length = 19
FEATURE                Location/Qualifiers
REGION                 1..19
                       note = Synthetic
source                 1..19
                       mol_type = protein
                       organism = synthetic construct
SEQUENCE: 31
PIILFINLKA LAALAKKIL                                                    19

SEQ ID NO: 32          moltype = AA   length = 19
FEATURE                Location/Qualifiers
REGION                 1..19
                       note = Synthetic
source                 1..19
                       mol_type = protein
                       organism = synthetic construct
SEQUENCE: 32
FIPLIINLKA LAALAKKIL                                                    19

SEQ ID NO: 33          moltype = AA   length = 19
FEATURE                Location/Qualifiers
REGION                 1..19
                       note = Synthetic
source                 1..19
                       mol_type = protein
                       organism = synthetic construct
SEQUENCE: 33
IPFLIINLKA LAALAKKIL                                                    19

SEQ ID NO: 34          moltype = AA   length = 19
FEATURE                Location/Qualifiers
REGION                 1..19
                       note = Synthetic
source                 1..19
                       mol_type = protein
                       organism = synthetic construct
SEQUENCE: 34
IIFLPINLKA LAALAKKIL                                                    19

SEQ ID NO: 35          moltype = AA   length = 19
FEATURE                Location/Qualifiers
REGION                 1..19
                       note = Synthetic
source                 1..19
                       mol_type = protein
                       organism = synthetic construct
SEQUENCE: 35
LIIFPINLKA LAALAKKIL                                                    19

SEQ ID NO: 36          moltype = AA   length = 19
FEATURE                Location/Qualifiers
REGION                 1..19
                       note = Synthetic
source                 1..19
                       mol_type = protein
                       organism = synthetic construct
SEQUENCE: 36
LFPIIINLKA LAALAKKIL                                                    19

SEQ ID NO: 37          moltype = AA   length = 19
FEATURE                Location/Qualifiers
REGION                 1..19
                       note = Synthetic
source                 1..19
                       mol_type = protein
```

```
                        -continued
SEQUENCE: 37
FLIPIINLKA LAALAKKIL                                                   19

SEQ ID NO: 38           moltype = AA   length = 19
FEATURE                 Location/Qualifiers
REGION                  1..19
                        note = Synthetic
source                  1..19
                        mol_type = protein
                        organism = synthetic construct
SEQUENCE: 38
PFIILINLKA LAALAKKIL                                                   19

SEQ ID NO: 39           moltype = AA   length = 19
FEATURE                 Location/Qualifiers
REGION                  1..19
                        note = Synthetic
source                  1..19
                        mol_type = protein
                        organism = synthetic construct
SEQUENCE: 39
IFIPLINLKA LAALAKKIL                                                   19

SEQ ID NO: 40           moltype = AA   length = 19
FEATURE                 Location/Qualifiers
REGION                  1..19
                        note = Synthetic
source                  1..19
                        mol_type = protein
                        organism = synthetic construct
SEQUENCE: 40
FILPIINLKA LAALAKKIL                                                   19

SEQ ID NO: 41           moltype = AA   length = 19
FEATURE                 Location/Qualifiers
REGION                  1..19
                        note = Synthetic
source                  1..19
                        mol_type = protein
                        organism = synthetic construct
SEQUENCE: 41
IILFPINLKA LAALAKKIL                                                   19

SEQ ID NO: 42           moltype = AA   length = 19
FEATURE                 Location/Qualifiers
REGION                  1..19
                        note = Synthetic
source                  1..19
                        mol_type = protein
                        organism = synthetic construct
SEQUENCE: 42
PLFIIINLKA LAALAKKIL                                                   19

SEQ ID NO: 43           moltype = AA   length = 19
FEATURE                 Location/Qualifiers
REGION                  1..19
                        note = Synthetic
source                  1..19
                        mol_type = protein
                        organism = synthetic construct
SEQUENCE: 43
FIPILINLKA LAALAKKIL                                                   19

SEQ ID NO: 44           moltype = AA   length = 19
FEATURE                 Location/Qualifiers
REGION                  1..19
                        note = Synthetic
source                  1..19
                        mol_type = protein
                        organism = synthetic construct
SEQUENCE: 44
IFPILINLKA LAALAKKIL                                                   19

SEQ ID NO: 45           moltype = AA   length = 19
FEATURE                 Location/Qualifiers
REGION                  1..19
                        note = Synthetic
source                  1..19
```

```
                          mol_type = protein
                          organism = synthetic construct
SEQUENCE: 45
IPILFINLKA LAALAKKIL                                              19

SEQ ID NO: 46             moltype = AA   length = 19
FEATURE                   Location/Qualifiers
REGION                    1..19
                          note = Synthetic
source                    1..19
                          mol_type = protein
                          organism = synthetic construct
SEQUENCE: 46
ILIPFINLKA LAALAKKIL                                              19

SEQ ID NO: 47             moltype = AA   length = 19
FEATURE                   Location/Qualifiers
REGION                    1..19
                          note = Synthetic
source                    1..19
                          mol_type = protein
                          organism = synthetic construct
SEQUENCE: 47
IFILPINLKA LAALAKKIL                                              19

SEQ ID NO: 48             moltype = AA   length = 19
FEATURE                   Location/Qualifiers
REGION                    1..19
                          note = Synthetic
source                    1..19
                          mol_type = protein
                          organism = synthetic construct
SEQUENCE: 48
IPIFLINLKA LAALAKKIL                                              19

SEQ ID NO: 49             moltype = AA   length = 19
FEATURE                   Location/Qualifiers
REGION                    1..19
                          note = Synthetic
source                    1..19
                          mol_type = protein
                          organism = synthetic construct
SEQUENCE: 49
IILPFINLKA LAALAKKIL                                              19

SEQ ID NO: 50             moltype = AA   length = 19
FEATURE                   Location/Qualifiers
REGION                    1..19
                          note = Synthetic
source                    1..19
                          mol_type = protein
                          organism = synthetic construct
SEQUENCE: 50
IPLIFINLKA LAALAKKIL                                              19

SEQ ID NO: 51             moltype = AA   length = 19
FEATURE                   Location/Qualifiers
REGION                    1..19
                          note = Synthetic
source                    1..19
                          mol_type = protein
                          organism = synthetic construct
SEQUENCE: 51
FIILPINLKA LAALAKKIL                                              19

SEQ ID NO: 52             moltype = AA   length = 19
FEATURE                   Location/Qualifiers
REGION                    1..19
                          note = Synthetic
source                    1..19
                          mol_type = protein
                          organism = synthetic construct
SEQUENCE: 52
FLIIPINLKA LAALAKKIL                                              19

SEQ ID NO: 53             moltype = AA   length = 19
FEATURE                   Location/Qualifiers
REGION                    1..19
                          note = Synthetic
```

```
source                    1..19
                          mol_type = protein
                          organism = synthetic construct
SEQUENCE: 53
PIFILINLKA LAALAKKIL                                                    19

SEQ ID NO: 54             moltype = AA   length = 19
FEATURE                   Location/Qualifiers
REGION                    1..19
                          note = Synthetic
source                    1..19
                          mol_type = protein
                          organism = synthetic construct
SEQUENCE: 54
FPIILINLKA LAALAKKIL                                                    19

SEQ ID NO: 55             moltype = AA   length = 19
FEATURE                   Location/Qualifiers
REGION                    1..19
                          note = Synthetic
source                    1..19
                          mol_type = protein
                          organism = synthetic construct
SEQUENCE: 55
FIIPLINLKA LAALAKKIL                                                    19

SEQ ID NO: 56             moltype = AA   length = 19
FEATURE                   Location/Qualifiers
REGION                    1..19
                          note = Synthetic
source                    1..19
                          mol_type = protein
                          organism = synthetic construct
SEQUENCE: 56
PIFLIINLKA LAALAKKIL                                                    19

SEQ ID NO: 57             moltype = AA   length = 19
FEATURE                   Location/Qualifiers
REGION                    1..19
                          note = Synthetic
source                    1..19
                          mol_type = protein
                          organism = synthetic construct
SEQUENCE: 57
FPLIIINLKA LAALAKKIL                                                    19

SEQ ID NO: 58             moltype = AA   length = 19
FEATURE                   Location/Qualifiers
REGION                    1..19
                          note = Synthetic
source                    1..19
                          mol_type = protein
                          organism = synthetic construct
SEQUENCE: 58
LPIFIINLKA LAALAKKIL                                                    19

SEQ ID NO: 59             moltype = AA   length = 19
FEATURE                   Location/Qualifiers
REGION                    1..19
                          note = Synthetic
source                    1..19
                          mol_type = protein
                          organism = synthetic construct
SEQUENCE: 59
PIIFLINLKA LAALAKKIL                                                    19

SEQ ID NO: 60             moltype = AA   length = 19
FEATURE                   Location/Qualifiers
REGION                    1..19
                          note = Synthetic
source                    1..19
                          mol_type = protein
                          organism = synthetic construct
SEQUENCE: 60
LFIPIINLKA LAALAKKIL                                                    19

SEQ ID NO: 61             moltype = AA   length = 19
FEATURE                   Location/Qualifiers
REGION                    1..19
```

```
                            note = Synthetic
source                      1..19
                            mol_type = protein
                            organism = synthetic construct
SEQUENCE: 61
ILPIFINLKA LAALAKKIL                                                   19

SEQ ID NO: 62               moltype = AA  length = 19
FEATURE                     Location/Qualifiers
REGION                      1..19
                            note = Synthetic
source                      1..19
                            mol_type = protein
                            organism = synthetic construct
SEQUENCE: 62
PILIFINLKA LAALAKKIL                                                   19

SEQ ID NO: 63               moltype = AA  length = 19
FEATURE                     Location/Qualifiers
REGION                      1..19
                            note = Synthetic
source                      1..19
                            mol_type = protein
                            organism = synthetic construct
SEQUENCE: 63
FPILIINLKA LAALAKKIL                                                   19

SEQ ID NO: 64               moltype = AA  length = 19
FEATURE                     Location/Qualifiers
REGION                      1..19
                            note = Synthetic
source                      1..19
                            mol_type = protein
                            organism = synthetic construct
SEQUENCE: 64
LIFPIINLKA LAALAKKIL                                                   19

SEQ ID NO: 65               moltype = AA  length = 24
FEATURE                     Location/Qualifiers
REGION                      1..24
                            note = Synthetic: Brevinin-1BLb
source                      1..24
                            mol_type = protein
                            organism = synthetic construct
SEQUENCE: 65
FLPIIAGVAA KVLPKIFCAI SKKC                                             24

SEQ ID NO: 66               moltype = AA  length = 24
FEATURE                     Location/Qualifiers
REGION                      1..24
                            note = Synthetic: Brevinin-1BLc
source                      1..24
                            mol_type = protein
                            organism = synthetic construct
SEQUENCE: 66
FLPIIAGIAA KFLPKIFCTI SKKC                                             24

SEQ ID NO: 67               moltype = AA  length = 24
FEATURE                     Location/Qualifiers
REGION                      1..24
                            note = Synthetic: Brevinin-1CHa
source                      1..24
                            mol_type = protein
                            organism = synthetic construct
SEQUENCE: 67
FLPIIAGVAA KVLPKLFCAI TKKC                                             24

SEQ ID NO: 68               moltype = AA  length = 24
FEATURE                     Location/Qualifiers
REGION                      1..24
                            note = Synthetic: Brevinin-1Pa
source                      1..24
                            mol_type = protein
                            organism = synthetic construct
SEQUENCE: 68
FLPIIAGVAA KVFPKIFCAI SKKC                                             24

SEQ ID NO: 69               moltype = AA  length = 24
FEATURE                     Location/Qualifiers
```

```
REGION                    1..24
                          note = Synthetic: Brevinin-1Pb
source                    1..24
                          mol_type = protein
                          organism = synthetic construct
SEQUENCE: 69
FLPIIAGIAA KVFPKIFCAI SKKC                                              24

SEQ ID NO: 70             moltype = AA  length = 24
FEATURE                   Location/Qualifiers
REGION                    1..24
                          note = Synthetic: Brevinin-1Pc
source                    1..24
                          mol_type = protein
                          organism = synthetic construct
SEQUENCE: 70
FLPIIASVAA KVFSKIFCAI SKKC                                              24

SEQ ID NO: 71             moltype = AA  length = 24
FEATURE                   Location/Qualifiers
REGION                    1..24
                          note = Synthetic: Brevinin-1Pd
source                    1..24
                          mol_type = protein
                          organism = synthetic construct
SEQUENCE: 71
FLPIIASVAA NVFSKIFCAI SKKC                                              24

SEQ ID NO: 72             moltype = AA  length = 24
FEATURE                   Location/Qualifiers
REGION                    1..24
                          note = Synthetic: Brevinin-1Pe
source                    1..24
                          mol_type = protein
                          organism = synthetic construct
SEQUENCE: 72
FLPIIASVAA KVFPKIFCAI SKKC                                              24

SEQ ID NO: 73             moltype = AA  length = 24
FEATURE                   Location/Qualifiers
REGION                    1..24
                          note = Synthetic: Brevinin-1Pf
source                    1..24
                          mol_type = protein
                          organism = synthetic construct
SEQUENCE: 73
FLPIIAGIAA KFLPKIFCAI SKKC                                              24

SEQ ID NO: 74             moltype = AA  length = 24
FEATURE                   Location/Qualifiers
REGION                    1..24
                          note = Synthetic: Brevinin-1Pk
source                    1..24
                          mol_type = protein
                          organism = synthetic construct
SEQUENCE: 74
FLPIIAGVAA KVFPKIFCTI SKKC                                              24

SEQ ID NO: 75             moltype = AA  length = 24
FEATURE                   Location/Qualifiers
REGION                    1..24
                          note = Synthetic: Brevinin-1Pl
source                    1..24
                          mol_type = protein
                          organism = synthetic construct
SEQUENCE: 75
FLPIIAGMAA KFLPKIFCAI SKKC                                              24

SEQ ID NO: 76             moltype = AA  length = 20
FEATURE                   Location/Qualifiers
REGION                    1..20
                          note = Synthetic: Brevinin-1SPb
source                    1..20
                          mol_type = protein
                          organism = synthetic construct
SEQUENCE: 76
FLPIIAGMAA KVICAITKKC                                                   20

SEQ ID NO: 77             moltype = AA  length = 24
```

```
FEATURE              Location/Qualifiers
REGION               1..24
                     note = Synthetic: Brevinin-1Yb
source               1..24
                     mol_type = protein
                     organism = synthetic construct
SEQUENCE: 77
FLPIIAGAAA KVVQKIFCAI SKKC                                          24

SEQ ID NO: 78        moltype = AA  length = 24
FEATURE              Location/Qualifiers
REGION               1..24
                     note = Synthetic: Brevinin-1Yc
source               1..24
                     mol_type = protein
                     organism = synthetic construct
SEQUENCE: 78
FLPIIAGAAA KVVEKIFCAI SKKC                                          24

SEQ ID NO: 79        moltype = AA  length = 13
FEATURE              Location/Qualifiers
REGION               1..13
                     note = Synthetic: Temporin-1AUa
source               1..13
                     mol_type = protein
                     organism = synthetic construct
SEQUENCE: 79
FLPIIGQLLS GLL                                                      13

SEQ ID NO: 80        moltype = AA  length = 13
FEATURE              Location/Qualifiers
REGION               1..13
                     note = Synthetic: Temporin-1BYa
source               1..13
                     mol_type = protein
                     organism = synthetic construct
SEQUENCE: 80
FLPIIAKVLS GLL                                                      13

SEQ ID NO: 81        moltype = AA  length = 13
FEATURE              Location/Qualifiers
REGION               1..13
                     note = Synthetic: Temporin-1DRc
source               1..13
                     mol_type = protein
                     organism = synthetic construct
SEQUENCE: 81
FLPIIASVLS SLL                                                      13

SEQ ID NO: 82        moltype = AA  length = 13
FEATURE              Location/Qualifiers
REGION               1..13
                     note = Synthetic: Temporin-1TGa
source               1..13
                     mol_type = protein
                     organism = synthetic construct
SEQUENCE: 82
FLPIIGKLLS GIL                                                      13

SEQ ID NO: 83        moltype = AA  length = 13
FEATURE              Location/Qualifiers
REGION               1..13
                     note = Synthetic: Temporin-PRb
source               1..13
                     mol_type = protein
                     organism = synthetic construct
SEQUENCE: 83
FLPIITNLLG KLL                                                      13

SEQ ID NO: 84        moltype = AA  length = 13
FEATURE              Location/Qualifiers
REGION               1..13
                     note = Synthetic: Vespid chemotactic peptide L
source               1..13
                     mol_type = protein
                     organism = synthetic construct
SEQUENCE: 84
FLPIIAKLVS GLL                                                      13
```

```
SEQ ID NO: 85              moltype = AA   length = 13
FEATURE                    Location/Qualifiers
REGION                     1..13
                           note = Synthetic: Vespid chemotactic peptide M
source                     1..13
                           mol_type = protein
                           organism = synthetic construct
SEQUENCE: 85
FLPIIGKLLS GLL                                                            13

SEQ ID NO: 86              moltype = AA   length = 13
FEATURE                    Location/Qualifiers
REGION                     1..13
                           note = Synthetic: Vespid chemotactic peptide X
source                     1..13
                           mol_type = protein
                           organism = synthetic construct
SEQUENCE: 86
FLPIIAKLLG GLL                                                            13
```

ANTIMICROBIAL PEPTIDES

CROSS-REFERENCE TO RELATED APPLICATIONS

This application claims benefit to U.S. Provisional Application No. 63/243,845, filed Sep. 14, 2021, the entire contents of which are incorporated herein by reference.

SEQUENCE LISTING

The instant application contains a sequence listing that has been submitted electronically in .XML format and is hereby incorporated by reference in its entirety. Said .XML copy, created on Sep. 14, 2022, is named 103241006873.xml and is 108,256 bytes in size.

TECHNICAL FIELD

The present disclosure pertains to peptides with antimicrobial properties.

BACKGROUND

The excessive use and misuse of antibiotics has led to increasing rates of resistance in pathogenic bacteria (1). According to the Centers for Disease Control and Prevention (CDC) report in 2019, 2.8 million antibiotic-resistant infections occur in the US each year, leading to approximately 35,000 deaths annually (2). In addition, 19.7% (~11 million) of all global deaths in 2017 were caused by sepsis, a syndrome most commonly linked to bacterial infections and for which antibiotics are the primary treatment (3). Drug-resistant infections are not only serious on their own. Secondary infections are also highly relevant and represent a major cause of death in global pandemics, being responsible for 95% of deaths during the 1918 flu pandemic (4) and also playing a role in the COVID-19 pandemic (5).

The emergence of multidrug-resistant bacterial pathogens has coincided with a severe decline in the development and approval of new antibacterial drugs (1). Thus, there is an urgent need for novel antibiotics effective against drug-resistant bacteria.

SUMMARY

Disclosed herein are antimicrobial peptides that comprise a mastoparan peptide having SEQ ID NO:1 and a pentapeptide motif formed from phenylalanine, leucine, proline, and two isoleucine residues, wherein the pentapeptide motif is conjugated the N-terminus of the mastoparan peptide.

Also provided are methods of treating a microbial infection in a subject comprising administering to the subject a therapeutically effective amount of an antimicrobial peptide according to the present disclosure.

The present disclosure also provides methods of removing a biofilm comprising contacting the biofilm with an effective amount of an antimicrobial peptide according to the present disclosure.

The present disclosure also pertains to methods of forming an antimicrobial peptide comprising conjugating a pentapeptide motif formed from phenylalanine, leucine, proline, and two isoleucine residues to a mastoparan peptide having SEQ ID NO:1 at the N-terminus of the peptide.

BRIEF DESCRIPTION OF THE DRAWINGS

The file of this patent or application contains at least one drawing/photograph executed in color. Copies of this patent or patent application publication with color drawings/photographs will be provided by the Office upon request and payment of the necessary fee.

FIG. 1A provides a schematic representation of the design approach based on FIG. 1B the insertion into the mast-L sequence of a pentapeptide motif (FLPII) conserved in naturally occurring peptides (e.g., brevenin, temporin and vespid chemotactic peptide families) with potent antimicrobial, immunomodulatory and chemotactic properties. Such insertion yielded the synthetic peptide mast-MO.

FIGS. 2A-2C pertains to analyses of the natural wasp venom toxin and its synthetic derivative. As provided in FIG. 2A, circular dichroism experiments showed that mast-L and mast-MO presented helical patterns in all tested media: DPC (15 mmol L−1), SDS (100 mmol L−1), TFE/Water (1/1, v/v), and PCPG (1 mmol L−1). The α-helical structures were confirmed by nuclear magnetic resonance. The TOCSY contour maps for mast-MO, as depicted in FIG. 2B, where the fingerprint region in $H_2O/D_2O$ (9:1, v/v) indicate a helical pattern. In FIG. 2C, the hydrogen by deuterium exchange experiment (H/D exchange) shows the orientation of mast-MO on the surface of SDS-d25 micelles. The slow H/D exchange demonstrated the high affinity between mast-MO and SDS micelles. Residues Ile4, Ala10, Leu11, Leu14, Lys17, Ile18 did not exchange the amide hydrogen for deuterium, because these amide groups are compromised interacting with the micelles. After seven days, residues Leu14 and Lys17 had not yet undergone H/D exchange, indicating that both residues may be in contact with the micelle or forming resistant hydrogen bonds thus preventing the H/D exchange (PDB ID: mastoparan-L—6DUL—and mastoparan-MO—6DUU).

FIG. 4A provides a schematic of different interactions displayed by mastoparan peptides on the surface of biological membranes leading to internalization into the cell and subsequent immunomodulatory effects. As shown in FIG. 4B, mast-MO (10 mg $Kg^{-1}$) triggered leukocyte recruitment to the E. coli ATCC8739 infection site to levels comparable to the positive control TGA, FIG. 4C shows release over time (48 h) of IL−12 and FIG. 4D depicts release over 48 h of TNF-α into the peritoneal cavity of mice. Cytokines monitored in mice for 24 h after infection with (as shown in FIG. 4E) E. coli ATCC8739 and (as shown in FIG. 4F) S. aureus ATCC29213. Cytokine release (i.e., IFN-γ, IL-6, IL−10, IL-12p70 and TNF-α) into the peritoneal cavity of C57BL/6 mice was detected and quantified 24 h after infection with E. coli ATCC8739 and S. aureus ATCC29213. In all experiments, mice were treated with 10 mg $Kg^{-1}$ of mastoparan-MO and 5 mg $Kg^{-1}$ of mastoparan-L. PBS and imipenem (10 mg $Kg^{-1}$) were used as negative and positive controls, respectively. Data were expressed as mean±standard deviation. Statistical analysis was performed using Bonferroni test. ***$p<0.001$ as significant compared to the control.

In FIG. 5A mice were infected with bacteria, treated with each peptide or antibiotic and monitored for 8 days. Survival and cell counts after 24 h, respectively, are shown for *E. coli* ATCC8739 ($2\times10^4$ CFU/mL inoculum) FIG. 5B and FIG. 5C, *S. aureus* ATCC29213 ($2\times10^9$ CFU/mL inoculum) FIG. 5D and FIG. 5E, *E. coli* 1812446 (KPC-positive) ($2\times10^4$ CFU inoculum) FIG. 5F and FIG. 5G, and *S. aureus* (MRSA) ATCC33591 ($2\times10^9$ CFU inoculum) FIG. 5H and FIG. 5I. Mice were treated intraperitoneally (i.p.) with 1, 5 and 10 mg $Kg^{-1}$ of mast-L, mast-MO or 10 mg $Kg^{-1}$ of the antibiotics gentamicin and imipenem. PBS was used as a control for the untreated group of mice. Treatments were administered 3 h post-infection. Data are expressed as the mean±standard deviation. Statistical analysis was performed using Bonferroni test. *p<0.1, p<0.01, *p<0.001 compared to the untreated control.

FIG. 6A provides a schematic showing the dual immunomodulatory and antimicrobial activities of mast-MO demonstrated in this work. The peptide killed bacterial cells by destabilizing their outer membrane and displayed immunomodulatory properties by attracting leukocytes to the site of infection and anti-inflammatory activity by repressing pro-inflammatory mediators (e.g., TNF-α and IL-12). Despite these therapeutic properties, mast-MO retained some cytotoxicity towards human cells at concentrations immediately above its antimicrobial and immunomodulatory activities hindering its use as a potential therapy in humans. FIG. 6B pertains to design of mast-MO derivatives through permutation of its FLPII motif. FIG. 6C depicts cytotoxic activity of mast-MO and its permutation variants against human embryonic kidney cells (i.e., HEK293). FIG. 6D provides a schematic of the experimental design. Briefly, the back of mice was shaved, and an abrasion was generated to damage the stratum corneum and the upper layer of the epidermis. Subsequently, an aliquot of 50 μL containing $5\times10^7$ CFU/20 μL of *P. aeruginosa* in PBS was inoculated over each defined area. One day post-infection, peptides (16 μmol $L^{-1}$) were administered to the infected area. In FIG. 6E, mouse body weight measurements throughout the experiment were taken and normalized by the body weight of non-infected mice as a proxy for potential toxicity. FIG. 6F illustrates the anti-infective activity of the permutation-based synthetic analogs compared to mast-MO-treated and negative control groups. Briefly, mice were anesthetized with isoflurane, had their backs shaved and a superficial linear skin abrasion was made with a needle in order to damage the stratum corneum and upper layer of the epidermis. A bacterial load $1\times10^7$ CFU/20 μL of bacteria (in 20 μL) in PBS was inoculated over each defined area containing the scratch with a pipette tip. One day after the infection, a single dose of each peptide (16 μmol $L^{-1}$) was administered to the infected area. Six animals per group were euthanized and the area of scarified skin was excised two days post-infection, homogenized using a bead beater for 20 min (25 Hz), and serially diluted for CFU quantification (statistical significance was determined using two-way ANOVA followed by Dunnett's test, ***p<0.001).

FIG. 8A depicts how most bacterial infections are present as surface-associated communities called biofilms. Biofilms are aggregates of microorganisms in which cells are embedded in a self-produced matrix of extracellular polymeric substrates that adhere to other aggregates or onto a surface (49). The biofilm state leads to overall increased antibiotic resistance profiles (50). Therefore, we tested whether mast-MO displayed antibiofilm activity using a dynamic flow cell apparatus as previously described (12, 51, 52). Glassy flow cells were colonized with *S. aureus* ATCC33591 and *E. coli* ATCC0157, and after 48 h were exposed to the peptide treatment or no treatment (untreated control). After 72 h, the medium flow was stopped, and cells were stained with SYTO-9 and propidium iodide (PI). Cell membranes were stained in green and dead cells were stained in red. Untreated flow cells colonized by (FIG. 8B) *S. aureus* and (FIG. 8E) *E. coli* showed slightly higher number of cells than the ones observed in the treated flow cells with mast-L as shown in FIG. 8C and FIG. 8F for *S. aureus* and *E. coli*, respectively. Mast-MO, on the other hand, showed high inhibition of biofilm formation, inhibiting almost completely the adhesion of cells to the glassy surface of the flow cells, FIG. 8D and FIG. 8G for *S. aureus* and *E. coli*, respectively.

DETAILED DESCRIPTION OF ILLUSTRATIVE EMBODIMENTS

Figure 3A:
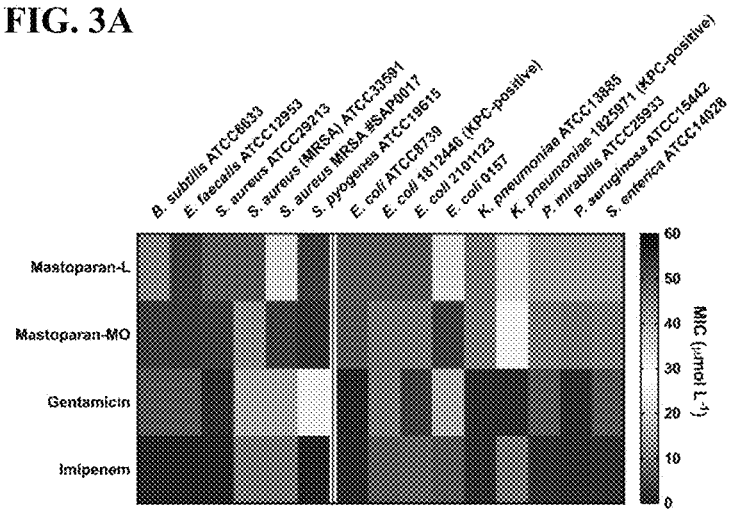
FIG. 3A depicts the antimicrobial activity of mast-L, mast-MO and standard-of-care antibiotics gentamicin and imipenem against 15 clinically relevant pathogens.

The presently disclosed inventive subject matter may be understood more readily by reference to the following detailed description taken in connection with the accompanying examples, which form a part of this disclosure. It is to be understood that these inventions are not limited to the specific formulations, methods, articles, or parameters described and/or shown herein, and that the terminology used herein is for the purpose of describing particular embodiments by way of example only and is not intended to be limiting of the claimed inventions.

The entire disclosures of each patent, patent application, and publication cited or described in this document are hereby incorporated herein by reference.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "an microbe" is a reference to one or more of such organisms and equivalents thereof known to those skilled in the art, and so forth. Furthermore, when indicating that a certain element "may be" X, Y, or Z, it is not intended by such usage to exclude in all instances other choices for the element.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" can refer to a value of 7.2 to 8.8, inclusive. This value may include "exactly 8". Where present, all ranges are inclusive and combinable. For example, when a range of "1 to 5" is recited, the recited range should be construed as optionally including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included."

In the present disclosure, numerals appearing in parentheses refer to the correspondingly numbered references that appear infra under the heading "References".

Toxins represent a previously untapped source of potential antimicrobials. They are contained in venoms and have evolved (e.g., in plants, animals and microbes) as part of defensive strategies. Typically, crude venoms contain a wide range of different peptide toxins, many of which are small in size, easy to synthesize, structurally stable, and highly biodiverse (6). Antimicrobial peptides (AMPs), a promising class of antibiotic candidates, have been found in venoms (7). AMPs have an almost unlimited sequence space and multiple mechanisms of action against microorganisms (1, 7-13). These agents can present broad- or narrow-spectrum activity, and rapid antimicrobial (7, 9, 10, 14) and immunomodulatory (11, 15-17) properties, which allow them to act against a range of microorganisms, including Gram-negative and Gram-positive bacteria, fungi, viruses, and parasites. Relevant to their potential clinical translatability, bacteria exposed to AMPs have been shown to develop resistance at a much lower rate than when exposed to conventional antibiotics (18).

Cationic peptides displaying an α-helical structure constitute a class of AMPs found in venoms. This class consists of small amphipathic peptides with net positive charge that tend to adopt an a-helical structure upon contact with hydrophilic/hydrophobic interfaces, such as the membrane of microorganisms (8). One such example is mast-L, an AMP from the mastoparan family, derived from the venom of the social wasp *Vespula lewisii*(19). The amino acid sequence of mast-L is NLKALAALAKKIL (SEQ ID NO:1). However, the use of this peptide as a therapeutic has been hindered by its toxicity profile, as it displays high hemolytic activity (13) and promotes massive mast cell degranulation (20, 21).

The present inventors have introduced modifications to mast-L in order to increase the therapeutic properties of the protein, while decreasing its inherent cytotoxicity. Through the approach disclosed herein, the inventors have generated novel anti-infective synthetic peptides that lack toxicity and display potent antimicrobial and immunomodulatory activities in clinically relevant sepsis and skin infection animal models.

Disclosed herein are antimicrobial peptides that comprise a mastoparan peptide having SEQ ID NO:1 and a pentapeptide motif formed from phenylalanine, leucine, proline, and two isoleucine residues, wherein the pentapeptide motif is conjugated the N-terminus of the mastoparan peptide.

Multidrug-resistant pathogens are becoming increasingly prevalent and no new classes of antibiotics have been discovered for decades. Therefore, strategies enabling the discovery of new strategies for treating infections are urgently needed. Toxins from the venom of insects and arthropods are rich in antimicrobials that represent an untapped source of template molecules for the design of novel drug candidates. The present inventors have leveraged a design strategy to convert a highly toxic peptide derived from wasp venom, namely, the mast-L protein from *Vespula lewisii*, into non-toxic synthetic derivatives with drug-like properties and anti-infective activity in pre-clinical animal models. Initially, a pentapeptide motif highly conserved in existing chemotactic and antimicrobial peptides was engineered into mast-L. In relation to mast-L, the resulting synthetic peptide, dubbed mast-MO, presented enhanced antimicrobial activity by destabilizing the bacterial outer membrane, and exhibited immunomodulatory properties by increasing leukocyte migration to the infection site and repressing pro-inflammatory factors, crucial to allow infection clearance. In animal models, mast-MO treatment caused a decrease in pro-inflammatory cytokines IL-12, TNF-α and IL-6 at the site of infection and increased leukocyte migration required for infection resolution. Since mast-MO retained some toxicity against human cells, the inventors also built, via permutation design, a second generation of analogs (FIG. 6). Seven identified synthetic peptides were no longer toxic against human cells and presented increased anti-infective activity against clinically relevant bacteria both in vitro and in vivo (FIG. 6).

The dual antimicrobial and immunomodulatory actions of mast-MO enable it to directly kill bacterial pathogens and selectively enhance host immune responses to clear infections while maintaining control of the inflammatory response. Multifunctional antimicrobials such as the ones presented here represent a new paradigm for treating infections by targeting both bacteria and the host. Moreover, the peptide did not induce any apparent immunotoxicities in any of the mouse models tested.

In some embodiments, the antimicrobial peptide comprises any one of SEQ ID NOS:5-64, as provided in Table 7, infra. In particular embodiments, the antimicrobial peptide comprises SEQ ID NO:19, SEQ ID NO:20, SEQ ID NO:31, SEQ ID NO:38, SEQ ID NO:52, SEQ ID NO:54, or SEQ ID NO:59.

The present disclosure also provides compositions for treating a microbial infection comprising a therapeutically effective amount of an antimicrobial peptide according to any one of the embodiments described herein. Also provided herein are methods of treating a microbial infection in a subject comprising administering to the subject a therapeutically effective amount of an antimicrobial peptide according to the present disclosure. As described above, the present inventors have discovered that the antimicrobial peptides disclosed herein possess antimicrobial characteristics, with better biocompatibility than the mast-L peptide, and therefore represent alternatives both to traditional antibiotic compounds to which microbial resistance has arisen or is likely to arise, and to naturally occurring AMPs that possess unacceptably high levels of toxicity to mammalian cells.

As used herein, the phrase "therapeutically effective amount" refers to the amount of active agent (here, the antimicrobial peptide) that elicits the biological or medicinal response that is being sought in a tissue, system, animal, individual or human by a researcher, veterinarian, medical doctor or other clinician, which includes one or more of the following:

(1) at least partially preventing the disease or condition or a symptom thereof; for example, preventing a disease, condition or disorder in an individual who may be predisposed to the disease, condition or disorder but does not yet experience or display the pathology or symptomatology of the disease;

(2) inhibiting the disease or condition; for example, inhibiting a disease, condition or disorder in an individual who is experiencing or displaying the pathology or symptomatology of the disease, condition or disorder (i.e., including arresting further development of the pathology and/or symptomatology); and (3) at least partially ameliorating the disease or condition; for example, ameliorating a disease, condition or disorder in an individual who is experiencing or displaying the pathology or symptomatology of the disease, condition or disorder (i.e., including reversing the pathology and/or symptomatology).

The antimicrobial peptides according to the present disclosure may be provided in a composition that is formulated for any type of administration. For example, the compositions may be formulated for administration orally, topically, parenterally, enterally, or by inhalation (e.g., intranasally). The active agent may be formulated for neat administration, or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspending/dispersing agent, tablet-disintegrating agent, encapsulating material, film former or coating, flavoring agent, or printing ink. Any material used in preparing any dosage unit form is preferably pharmaceutically pure and substantially non-toxic in the amounts employed. In addition, the active agent may be incorporated into sustained-release preparations and formulations. Administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active agent(s) in such therapeutically useful compositions is preferably such that a suitable dosage will be obtained.

Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients, for example, for oral, topical, or parenteral administration, include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active agents can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like.

In some instances, the antimicrobial peptides themselves may be sufficient to prevent contamination by microorganisms. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active agent in the pharmaceutically appropriate amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and freeze drying techniques that yield a powder of the active ingredient or ingredients, plus any additional desired ingredient from the previously sterile-filtered solution thereof.

Thus, an antimicrobial peptide may be in the present compositions and methods in an effective amount by any of the conventional techniques well-established in the medical field. For example, the administration may be in the amount of about 0.1 mg/day to about 500 mg per day. In some embodiments, the administration may be in the amount of about 250 mg/kg/day. Thus, administration may be in the amount of about 0.1 mg/day, about 0.5 mg/day, about 1.0 mg/day, about 5 mg/day, about 10 mg/day, about 20 mg/day, about 50 mg/day, about 100 mg/day, about 200 mg/day, about 250 mg/day, about 300 mg/day, or about 500 mg/day.

Also disclosed are methods comprising contacting a biofilm with an effective amount of an antimicrobial peptide according to the present disclosure. Such methods may be effective to remove or reduce the presence of an unwanted biofilm, such as in hospitals or other medical settings, in sewer and filtration systems, in industrial settings, on equipment involved in food preparation or manufacture, in aquaculture or hydroponics, or in any other context that is prone to unwanted biofilm formation.

In accordance with the methods of treating a microbial infection in a subject or the methods comprising contacting a biofilm according to the present disclosure, microbes against which the present antimicrobial peptides are effective may be, for example, any unicellular organism, such as gram-negative bacteria, gram-positive bacteria, protozoa, viruses, bacteriophages, and archaea. The present peptides can have an antimicrobial effect with respect to any such microbe. Examples of bacteria against which the present compounds are effective to cause reduction in numbers include gram positive bacteria and gram negative bacteria, for example, *Salmonella enterica, Listeria monocytogenes, Escherichia coli, Clostridium botulinum, Clostridium difficile, Campylobacter, Bacillus cereus, Vibrio parahaemolyticus, Vibrio cholerae, Vibrio vulnificus, Staphylococcus aureus, Yersinia enterocolitica, Shigella, Moraxella* spp., *Helicobacter, Stenotrophomonas, Bdellovibrio, Legionella* spp. (e.g., *pneumophila*), *Neisseria gonorrhoeae, Neisseria meningitidis, Haemophilus influenzae, Acinetobacter baumannii, Klebsiella pneumoniae, Pseudomonas aeruginosa, Proteus mirabilis, Enterobacter cloacae, Serratia marcescens, Helicobacter pylori, Salmonella enteritidis, Salmonella typhi*, and combinations thereof. Examples of *Salmonella enterica* serovars that can be reduced using the compounds of the disclosure include, for example, *Salmonella enteriditis, Salmonella typhimurium, Salmonella poona, Salmonella heidelberg*, and *Salmonella anatum*. Exemplary viruses against which the present peptides are effective to cause reduction in numbers include coronaviruses, rhinoviruses, and influenza viruses.

Hereinafter, the present disclosure will be described in more detail through Examples, which are intended to be illustrative to the present disclosure, although present disclosure is not limited to the Examples.

Example 1—Generation of Novel Antimicrobial Peptides

Design and structural analyses of wasp venom derived peptides. Despite the promise of mast-L as an antimicrobial, its activity must be improved to surpass that of standard-of-care antibiotics in order to enter clinical trials. In order to increase its antimicrobial and immunomodulatory properties, we performed a comprehensive search and analysis of the Antimicrobial Peptides Database (APD3)(22) looking for conserved motifs associated with such biological functions. The pentapeptide motif (FLPII) was identified to be conserved in the N-terminal extremity of peptides with high antimicrobial and immunomodulatory (e.g., chemotactic) activities, including brevenins (23, 24), temporins (24), vespid chemotactic peptides (25) (FIG. 1A and Table 1) and mediating interactions with membranes in plant lipocalins (26).

TABLE 1

Natural peptides with potent antimicrobial and immunomodulatory activities containing the conserved FLPII pentapeptide motif in their N-terminal extremity.

| Family | Peptide | SEQ ID NO | Sequence |
| --- | --- | --- | --- |
| Brevenins | Brevinin-1BLb | 65 | FLPIIAGVAAKVLPKIFCAISKKC |
| | Brevinin-1BLc | 66 | FLPIIAGIAAKFLPKIFCTISKKC |
| | Brevinin-1CHa | 67 | FLPIIAGVAAKVLPKLFCAITKKC |
| | Brevinin-1Pa | 68 | FLPIIAGVAAKVFPKIFCAISKKC |
| | Brevinin-1Pb | 69 | FLPIIAGIAAKVFPKIFCAISKKC |
| | Brevinin-1Pc | 70 | FLPIIASVAAKVFSKIFCAISKKC |
| | Brevinin-1Pd | 71 | FLPIIASVAANVFSKIFCAISKKC |
| | Brevinin-1Pe | 72 | FLPIIASVAAKVFPKIFCAISKKC |
| | Brevinin-1Pf | 73 | FLPIIAGIAAKFLPKIFCAISKKC |
| | Brevinin-1Pk | 74 | FLPIIAGVAAKVFPKIFCTISKKC |
| | Brevinin-1Pl | 75 | FLPIIAGMAAKFLPKIFCAISKKC |
| | Brevinin-1SPb | 76 | FLPIIAGMAAKVICAITKKC |
| | Brevinin-1Yb | 77 | FLPIIAGAAAKVVQKIFCAISKKC |
| | Brevinin-1Yc | 78 | FLPIIAGAAAKVVEKIFCAISKKC |
| Temporins | Temporin-1AUa | 79 | FLPIIGQLLSGLL |
| | Temporin-1BYa | 80 | FLPIIAKVLSGLL |
| | Temporin-1DRc | 81 | FLPIIASVLSSLL |
| | Temporin-1TGa | 82 | FLPIIGKLLSGIL |
| | Temporin-PRb | 83 | FLPIITNLLGKLL |
| Vespid Chemotactic Peptides | Vespid chemotactic peptide L | 84 | FLPIIAKLVSGLL |
| | Vespid chemotactic peptide M | 85 | FLPIIGKLLSGLL |
| | Vespid chemotactic peptide X | 86 | FLPIIAKLLGGLL |

In order to design a synthetic peptide with increased biological activity, the motif FLPII was engineered into the N-terminal extremity of mast-L (FIG. 1B), as changes in this part of the sequence are known to lead to loss of toxicity towards neutral vesicles mimicking human cell membranes (27) (Table 1).

Mastoparans, like other helical AMPs, are unstructured in aqueous solution and tend to structure into an α-helix upon contact with hydrophobic/hydrophilic interfaces, such as the one between bacterial membranes and the surrounding environment. The antimicrobial activity of such AMPs correlates with their ability to undergo the structural conformation change from unstructured to helical (7), and even small modifications to their sequence impact their structural tendency and biological activity. In order to assess whether insertion of the FLPII motif affected peptide structure, we elucidated the 3D structure of both mast-L and mast-MO through circular dichroism (CD—FIG. 2A) and of mast-MO using nuclear magnetic resonance (NMR—FIGS. 2B-2C and Table 2).

TABLE 2

Cytotoxic activity profile of mast-MO and mast-L. The cytotoxicity of the peptides was evaluated against human red blood cells (hRBCs), murine fibroblasts (L929), murine macrophages monocytes (RAW 264.7), and human embryonic kidney (HEK293) cells.

| | Peptide Concentration (μmol L$^{-1}$) | | | | |
|---|---|---|---|---|---|
| Cell Line | Mast-L | Mast-MO | LL-37 | Gentamicin | Imipenem |
| hRBCs | 7 | >400 | 87 | >400 | >400 |
| HEK293 | 50 | 25 | NT | NT | NT |
| L929 | 10 | >400 | 95 | >400 | >400 |
| RAW 264.7 | 10 | >400 | 100 | >400 | >400 |

NT—Not tested.

The CD experiments indicated that both peptides (FIG. 2) presented well-defined helical structures in the presence of TFE/Water (1:1; v:v), sodium dodecyl sulphate (SDS, 100 mmol L$^{-1}$) micelles and phospholipid vesicles. The positive band around 192-193 nm and two negative bands at 208 and 222 nm (FIG. 2A) observed for both, mast-L and mast-MO, are characteristic profiles of α-helical structures (28). The highest α-helical content values, recorded for both peptides, was in SDS micelles (75.0% for mast-L and 79.5% for mast-MO), indicating that they undergo coil-helical transition upon contact with hydrophobic/hydrophilic interfaces, such as bacterial membranes. The same behavior was observed when peptides were added to other hydrophobic/hydrophilic interfaces such as dodecylphosphocholine (DPC) vesicles, trifluoroethanol (TFE)/Water mixture (3:2, v:v), and 1-palmitoyl-2-oleoyl-sn-glycero-3-phosphocholine (POPC): 1-palmitoyl-2-oleoyl-sn-glycero-3-phosphoglycerol (POPG) (3:1, 10 mmol L$^{-1}$) vesicle.

The a-helical structure of mast-MO was confirmed by 2D-NMR spectroscopy in deuterated SDS-d$_{25}$ micelles (100 mmol L$^{-1}$). The $^1$H resonance assignments were performed by simultaneous analyses of the TOCSY and NOESY contour maps (FIGS. 2B-2C), as previously described (29). The structural statistics for low-energy structures are detailed in Table 3.

TABLE 3

NMR and refinement statistics for peptide structures.

| | Mast-L | Mast-MO |
|---|---|---|
| NMR distance and dihedral constraints | | |
| Distance constraints | | |
| Total NOE | 219 | 221 |
| Intra-residue | 135 | 101 |
| Inter-residue | | |
| Sequential (\|i − j\| = 1) | 72 | 113 |
| Medium-range (\|i − j\| < 4) | 12 | 7 |
| Long-range (\|i − j\| > 5) | 0 | 0 |
| Intermolecular | | |
| Hydrogen bonds | 0 | 0 |
| Total dihedral angle restraints | | |
| ϕ | 12 | 17 |
| ψ | 12 | 17 |
| Structure statistics | | |
| Violations (mean and s.d.) | | |
| Distance constraints (Å) | 0.462 ± 0.011 | 0.525 ± 0.019 |
| Dihedral angle constraints (°) | 0.343 ± 0.029 | 0.387 ± 0.028 |
| Max. dihedral angle violation (°) | 0.386 | 0.415 |
| Max. distance constraint violation (Å) | 0.483 | 0.557 |
| Deviations from idealized geometry | | |
| Bond lengths (Å) | 0.018 ± 0.002 10$^{-4}$ | 0.018 ± 0.002 10$^{-4}$ |
| Bond angles (°) | 0.462 ± 0.001 | 0.525 ± 0.003 |
| Impropers (°) | 0.343 ± 0.007 | 0.392 ± 0.005 |
| Average pairwise RMS deviation** (Å) | | |
| Heavy | 1.35 ± 0.31 | 1.42 ± 0.35 |
| Backbone | 0.76 ± 0.25 | 0.98 ± 0.30 |

**Pairwise RMS deviation was calculated among ten refined structures for residues 1 to 14 for mast-L and 1 to 19 for mast-MO.

The secondary structure of the peptides was predicted by chemical shift index (CSI) using NMRView, and the experimental chemical shifts of H$_\alpha$, C$_\alpha$, H$_N$ and N. CSI showed a well-defined α-helical structure throughout the whole sequence (between Leu$^3$ and Leu$^{14}$ residues) of mast-L and the maintenance of this helical behavior in mast-MO even with the additional of the pentapeptide motif (between Ile$^5$ and Ile$^{17}$ residues). The α-helical structure was confirmed using of the TALOS+ software, in which the dihedral angles were estimated, phi (ϕ) and psy (ψ) torsion angles (Table 4) of the peptide backbone and classified the values obtained as consistent with the predicted structures by CSI.

TABLE 4

Dihedral angle generated by the TALOS+.

| Residue number | Mast-L | | Mast-MO | |
|---|---|---|---|---|
| | Phi (φ) | Psi (ψ) | Phi (φ) | Psi (ψ) |
| 1 | — | — | — | — |
| 2 | −81.987 | −137.277 | −98.083 | 115.394 |
| 3 | −61.350 | −33.718 | −60.487 | 145.120 |
| 4 | −59.595 | −42.256 | −62.650 | −24.572 |
| 5 | −63.924 | −41.425 | −85.539 | −16.800 |
| 6 | −63.458 | −40.117 | −76.246 | −25.646 |
| 7 | −62.957 | −36.890 | −62.929 | −40.922 |
| 8 | −64.029 | −41.696 | −66.947 | −35.670 |
| 9 | −64.223 | −42.331 | −64.311 | −44.022 |
| 10 | −60.986 | −42.934 | −67.299 | −39.006 |
| 11 | −59.767 | −35.453 | −64.754 | −42.410 |
| 12 | −68.999 | −36.486 | −65.695 | −36.129 |
| 13 | −80.440 | −24.618 | −65.879 | −39.182 |
| 14 | — | — | −68.137 | −35.730 |

TABLE 4-continued

Dihedral angle generated by the TALOS+.

| Residue number | Mast-L | | Mast-MO | |
|---|---|---|---|---|
| | Phi (φ) | Psi (ψ) | Phi (φ) | Psi (ψ) |
| 15 | | | −61.299 | −41.414 |
| 16 | | | −65.871 | −34.946 |
| 17 | | | −71.030 | −35.612 |
| 18 | | | −83.630 | −16.631 |
| 19 | | | — | — |

Mastoparan peptides depend on their helical structure to exert antimicrobial activity (7). After initial electrostatic interactions with the membrane, this class of peptides tend to adopt an amphipathic helical structure with well-defined hydrophobic and hydrophilic faces upon contact with the phospholipids present on the membrane lipid bilayer, leading to membrane destabilization. Thus, the structural data showed that mast-MO preserved the helical tendency of mast-L, a critical requirement for these peptides to display antimicrobial activity.

Figure 6A:
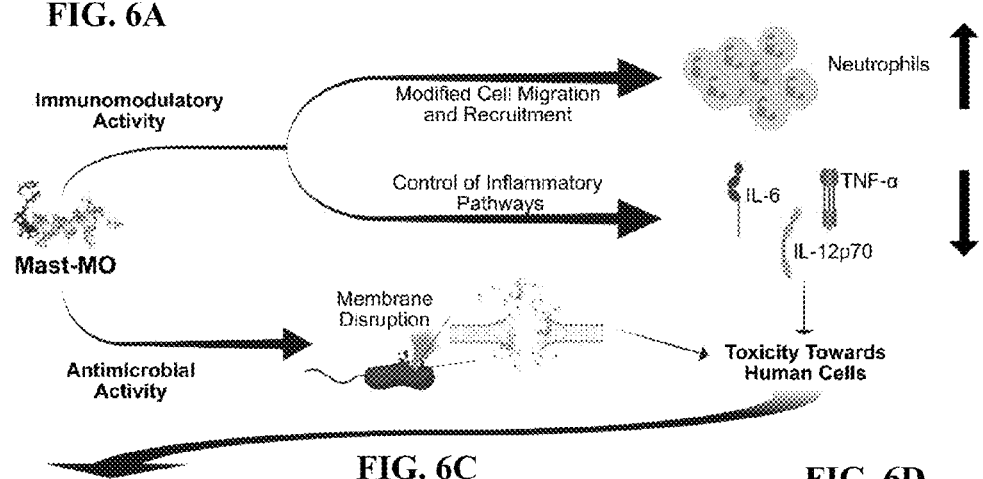
FIG. 6A-6F pertain to a study demonstrating that permutations of the conserved motif lead to mast-MO variants that lack toxicity against human cells and display anti-infective activity in a mouse model.
Figure 6B:
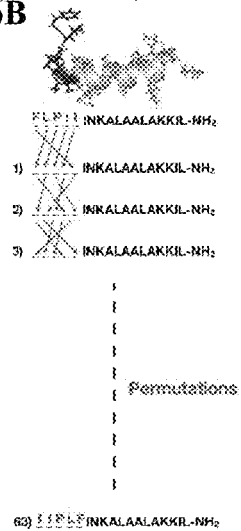
Figure 6C:
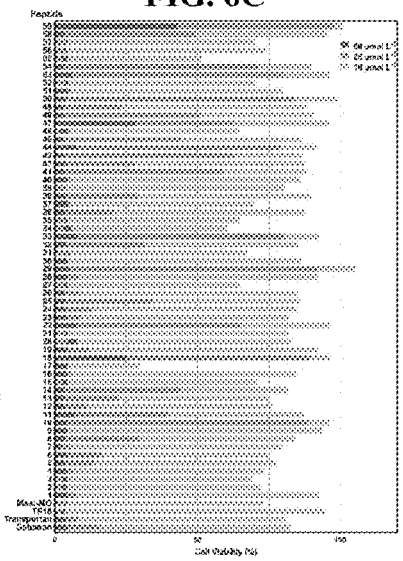
Figure 6D:
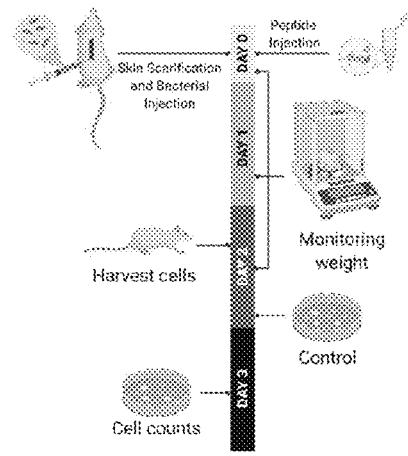
Figure 6E:
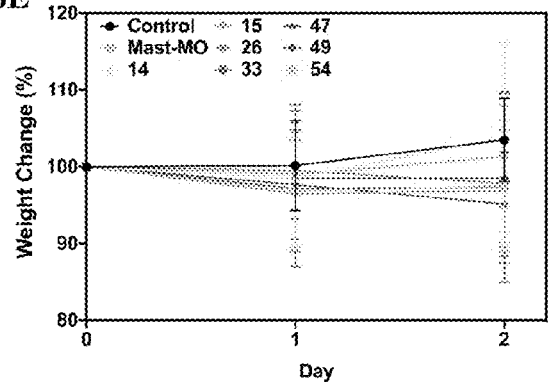
Figure 6F:
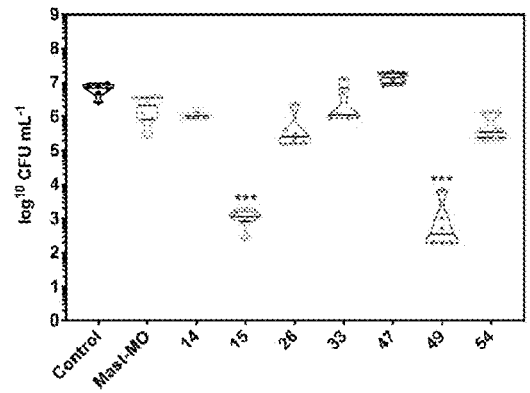
Figure 7:
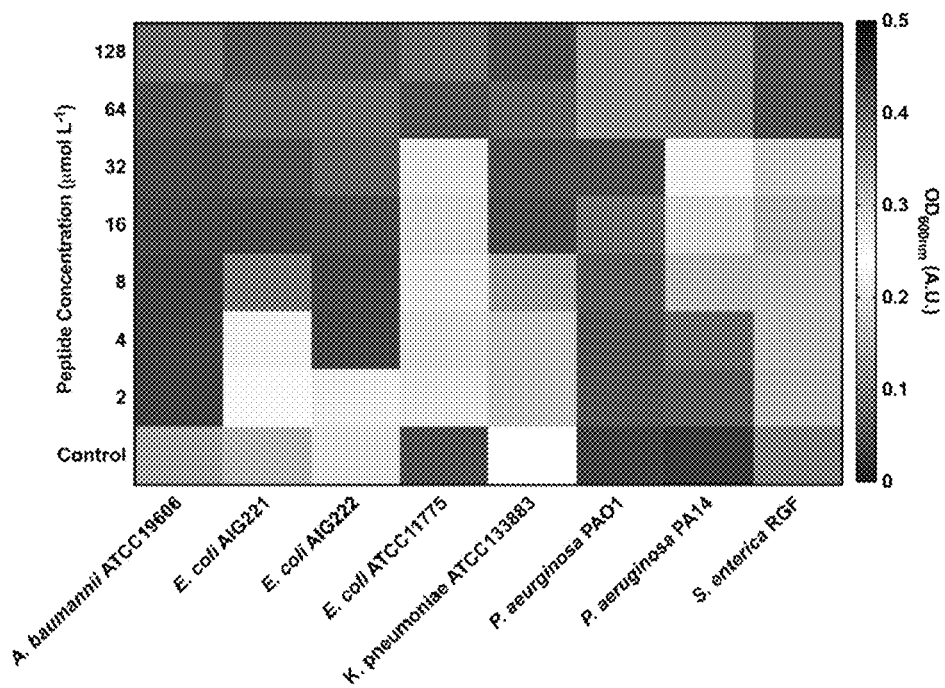
FIG. 7 illustrates the antimicrobial activity of Mast-MO against clinically relevant Gram-negative bacterial strains. Two-fold dilutions of peptide ranging from 0 to 128 μmol $L^{-1}$ in LB medium were added to 96-wells and exposed to $10^5$ bacterial cells and incubated for 24 h at 37° C. The optical density at 600 nm ($OD_{600}$) was measured in a microplate reader after 24 h (red meaning very low or absent growth and blue meaning growth of bacterial cells). Experiments were performed in three biological replicates.
Figure 8A:
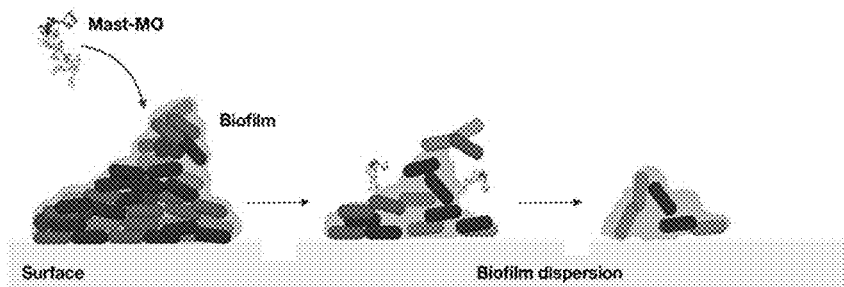
FIGS. 8A and 8B illustrate the anti-biofilm activity of mast-MO.
Figure 8B:
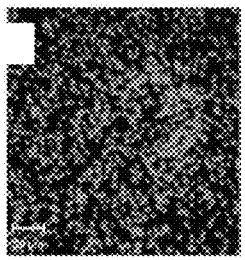
Figure 8C:
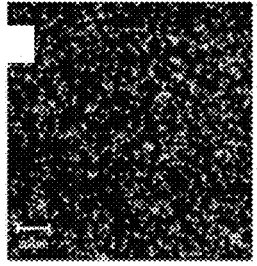
Figure 8D:
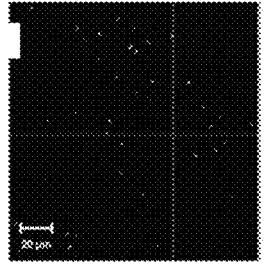
Figure 8E:
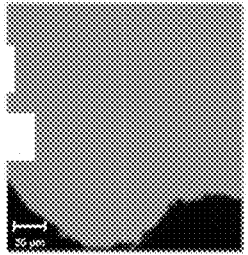
Figure 8F:
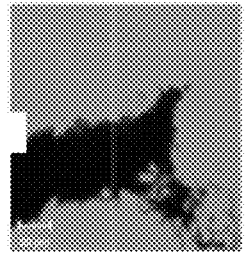
Figure 8G:
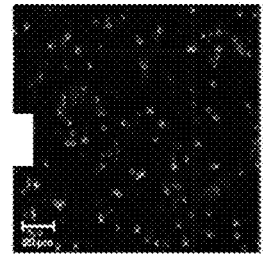

Example 2—Assessment of Antimicrobial Activity, Immunomodulatory Effect, and Cytotoxicity Synthetic peptide mast-MO exhibits decreased toxicity, and increased antimicrobial and immunomodulatory activities compared to parent wasp venom toxin mast-L. Helical conformations are known to be crucial for the antimicrobial activity of mastoparans (7). Once it was confirmed that insertion of the conserved pentapeptide motif FLPII did not alter the helical tendency of the peptide, a series of bacterial growth inhibition assays were performed in vitro to evaluate whether the motif influenced biological function. First, we assessed the minimal inhibitory concentration (MIC) of the peptide against 15 pathogens (FIG. 3A and FIG. 7). Pathogenic bacteria, including members of the ESKAPE list of the World Health Organization (2) and antibiotic-resistant strains, were exposed to increasing concentrations of the peptides for 24 h. Overall, mast-MO presented a similar activity profile, though slightly superior, compared to its predecessor mast-L, and increased activity with respect to two standard-of-care antibiotics (gentamicin and imipenem) (FIG. 3A). Briefly, mast-MO presented increased activity against Gram-positive bacteria compared to Gram-negatives and it was slightly more effective than mast-L against the majority of strains tested, with the exceptions of S. aureus MRSA, E. coli (2101123), E. coli 0157 and K. pneumoniae 1825971 (KPC971). Mast-MO (4 μg mL$^{-1}$) also exhibited increased antibiofilm properties against E. coli ATCC0157 and S. aureus ATCC33591 compared to mast-L both in vitro (FIG. 8) and in vivo (FIG. 6F).

Figure 3B:
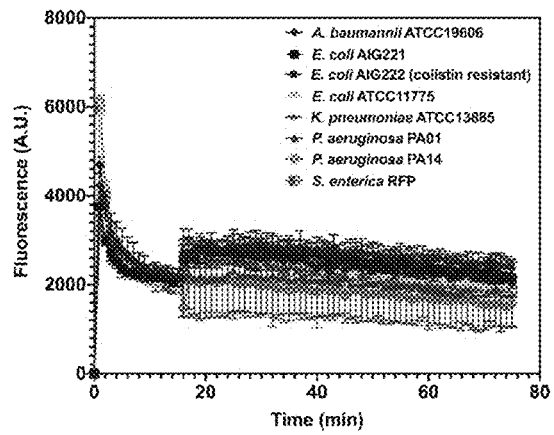
FIG. 3B shows the cytoplasmic membrane depolarization effects of mast-MO against 8 different Gram-negative pathogens determined using the $DiSC_3(5)$ assay and FIG. 3C provides an NPN assay demonstrating the ability of mast-MO to potently damage and permeabilize the bacterial outer membrane compared to the controls in the absence of mast-MO.
Figure 3C:
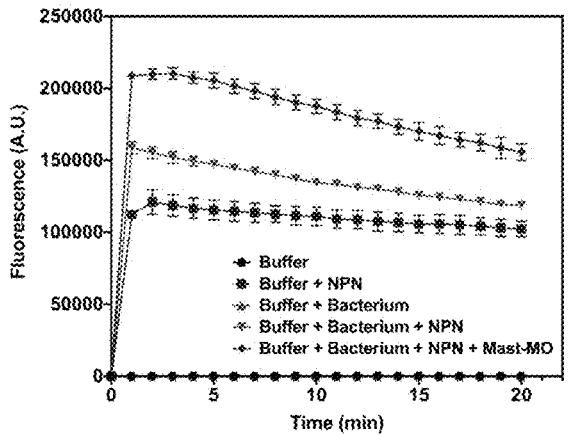
Figure 9:
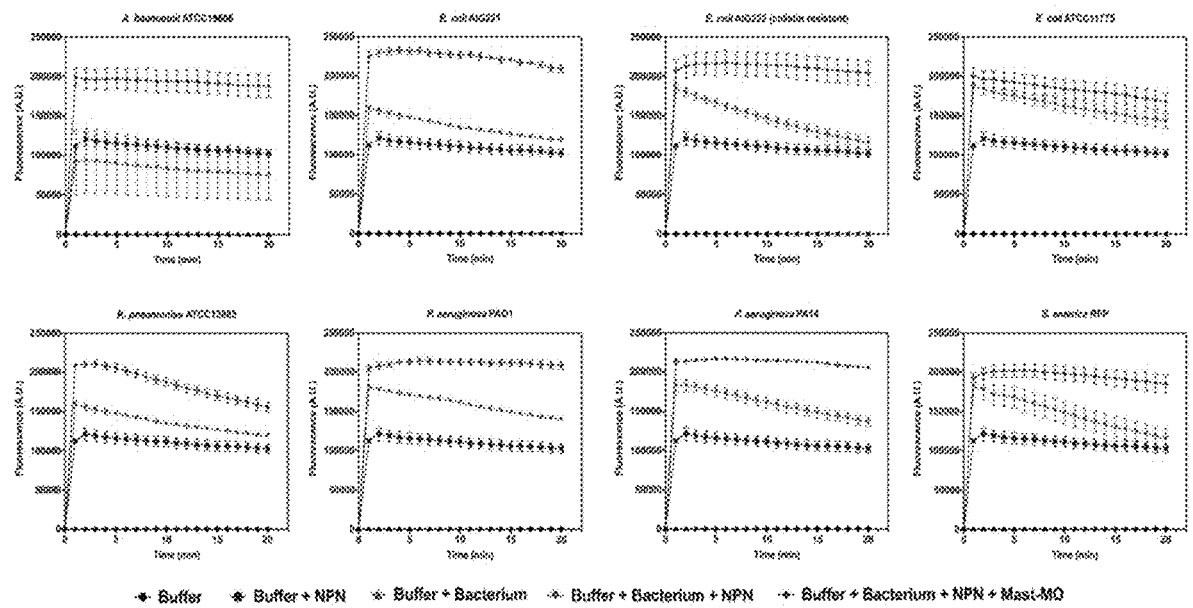
FIG. 9 depicts the results of bacterial outer membrane permeabilization assays using the hydrophobic dye NPN. Briefly, the membrane permeability of each bacteria exposed to mast-MO (20 μmol $L^{-1}$) was determined by using the N-phenyl-1-napthylamine (NPN) uptake assay. Bacteria were grown to $OD_{600}$ of 0.4, centrifuged (10,000 rpm at 4° C. for 10 min), washed and resuspended in buffer (5 mmol $L^{-1}$ HEPES, 5 mmol $L^{-1}$ glucose, pH 7.4). Four 4 of NPN solution (0.5 mmol $L^{-1}$—working concentration of 10 μmol $L^{-1}$ after dilutions) was added to 1004 of bacterial solution in white 96-well plates. The background fluorescence was recorded at $\lambda_{ex}=350$ nm and $\lambda_{em}=420$ nm. Mast-MO samples in water (1004 solution at 1.2 μmol $L^{-1}$) were added to the 96-wells plate, and fluorescence was recorded as a function of time until no further increase in fluorescence was observed (at 20 min). Mast-MO was able to disturb the outer membrane of all bacteria tested by permeabilization.

Mastoparans are known to act through several mechanisms of action (13, 19-21, 30-32), and even minor modifications to their sequence have been shown to lead to different activity profiles (13, 31, 32). In order to gain insights into the mechanisms of action by which these peptides kill bacterial cells, we used the probes 3,3'-dipropylthiadicarbocyanine iodide [DiSC$_3$(5)] and 1-(N-phenylamino)-naphthalene (NPN) to assess whether mast-MO was capable of depolarizing the cytoplasmic membrane and/or permeabilizing the outer membrane of bacteria, respectively. DiSC$_3$(5) is a potentiometric fluorophore that accumulates in the cytoplasmic membrane of bacterial cells. When the accumulation of DiSC$_3$(5) molecules reaches a certain threshold, those molecules aggregate, quenching their fluorescence. Upon disbalances on the transmembrane potential of the membrane, the fluorophore migrates to the cytoplasm or the outer environment, fluorescing again. In these assays, mast-MO only mildly depolarized the cytoplasmic membrane of 8 different clinically relevant Gram-negative bacterial strains (FIG. 3B), against which we had observed antimicrobial activity (FIG. 7). On the other hand, mast-MO potently permeabilized the outer membrane of the same set of 8 bacterial strains (FIG. 3C and FIG. 9) as determined by increased fluorescence of the lipophilic dye NPN in the NPN assay. NPN generates weak fluorescence in aqueous environments and is unable to permeate bacterial membranes unless they are damaged, but its fluorescence increases upon contact with lipidic environments such as the interior of the lipid bilayers of bacterial membranes therefore indicating that the membrane has been permeabilized and is thus compromised.

Once the mechanisms by which the peptide targeted bacterial cells was elucidawted, the effect of the pentapeptide motif insertion on cytotoxicity against mammalian cells was evaluated. Mast-MO did not present hemolytic activity in human red blood cell assays at the concentration range tested (1-400 μmolL$^{-1}$), but it was toxic at 25 μmolL$^{-1}$ against the human embryonic cell line HEK293, whereas mast-L was both hemolytic and toxic towards the different human and m-urine cell lines tested at 7-50 μmolL$^{-1}$ (Table 2). Interestingly, mast-MO was not cytotoxic when incubated with mouse cell lines such as murine fibroblasts (L929 cells) and murine macrophages (RAW 264.7 cells) (Table 2). Therefore, the anti-infective activity of mast-MO was then tested in pre-clinical mouse models. First, the toxicity of a single dose of either mast-L or mast-MO administered peritoneally to mice was assessed in order to determine the range of concentrations to be used in subsequent animal experiments. The hemolytic activity of mast-MO (up to 200 μmolL$^{-1}$) against murine red blood cells (Table 6) was also tested prior to conducting animal experiments. In preliminary mouse experiments, mast-L was highly toxic at concentrations higher than 10 mg Kg$^{-1}$ whereas mast-MO lacked toxicity (Table 5), in line with the presently disclosed results using mouse cell lines (Table 2).

TABLE 5

Evaluation of gross toxicity in mice treated with mastoparan-L and mastoparan-MO. Each mouse was injected with the indicated dose in 0.5 mL of peptide solution in PBS. Five animals per group were directly inspected for adverse effects for 30 min, and mortality was monitored during 6 h.

| Dose (mg Kg$^{-1}$) | Imipenem [number of mice (TL)] | Mast-L [number of mice (TL)] | Mast-MO [number of mice (TL)] |
|---|---|---|---|
| 0 | — | — | — |
| 1 | — | — | — |
| 5 | — | 2 (TL-1) | — |
| 10 | — | 5 | — |
| 30 | — | X | — |
| 50 | 2 (TL-1) | X | — |
| 90 | 3 (TL-2) | X | 2 (TL-1) |

— No observed effect, X all animals were dead, TL—Toxicity level: 1, narrowing of eyes; 2, crouching and cuddling. Most mice recovered 2 h after treatment.

TABLE 6

Evaluation of the hemolytic and cytotoxic activities of the motif (FLPII) inserted in the N-terminal extremity of the synthetic peptide mastoparan-MO. The hemolytic activity of mastoparan-MO against mouse red blood cells (mRBCs) was assessed by exposing the cells to peptide solutions ranging from 0.5 to 200 μmol L$^{-1}$. 0.1% Triton X-100 was used as positive control (100% hemolysis) and the human cathelicidin LL-37 was used for comparison. The release of hemoglobin was measured at 550 nm and expressed as percentage of lysed cells. The cytotoxic activity of mastoparan-MO and LL-37 against RAW 264.7 monocytes was performed by incubating the cells for 24 h with peptide solutions ranging from 0.5 to 200 μmol L$^{-1}$ and observing cell viability using MTT assays. The data shown represent the mean of three biological replicates.

| Cells type | Peptide Concentration (μmol L$^{-1}$) | |
|---|---|---|
| | FLPII motif | LL-37 |
| RAW 264.7 | >200 | 100 |
| mRBCs | >200 | 100 |

Based on these results, concentrations ranging from 1 to 10 mg Kg$^{-1}$ of mast-MO and 1 to 5 mg Kg$^{-1}$ of mast-L were used, which are not cytotoxic, in subsequent experiments.

Figure 5A:
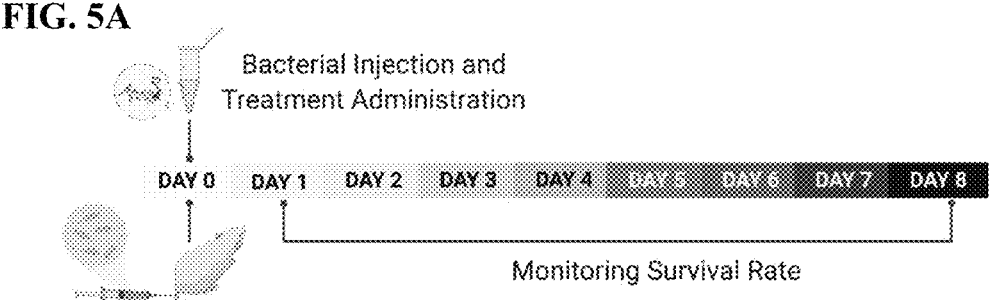
FIG. 5A-5I pertains to a study of the anti-infective activity of mast-MO against Gram-negative and Gram-positive pathogens in a lethal sepsis infection model.
Figure 5B:
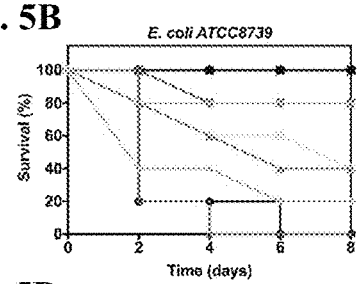
Figure 5C:
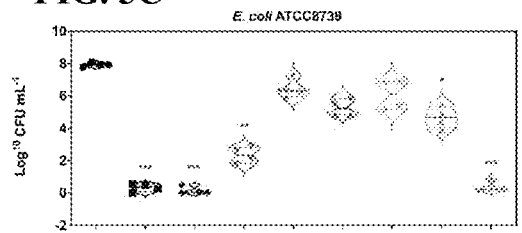
Figure 5D:
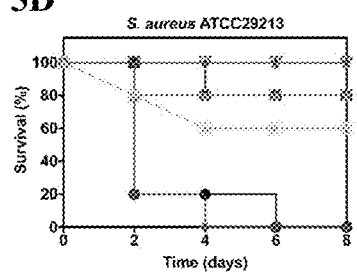
Figure 5E:
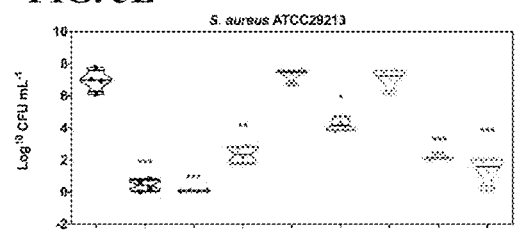
Figure 5F:
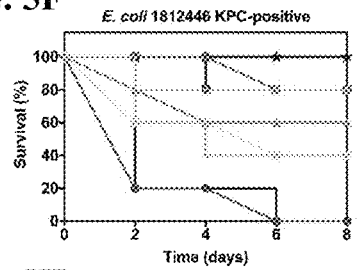
Figure 5G:
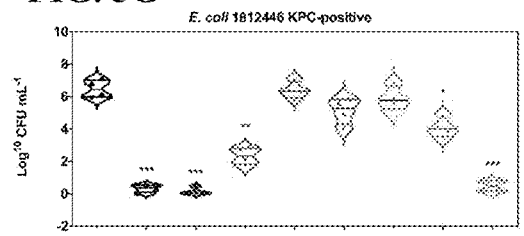

To test whether the FLPII motif within the mast-MO sequence led to increased immunomodulatory and chemotactic properties with respect to mast-L, ELISA experiments were performed using the peritoneal fluid collected from mice (FIG. 5a). C57BL/6 mice were infected with both Gram-negative and Gram-positive pathogens and administered either mast-L or mast-MO intraperitoneally. For mice infected with *E. coli* ATCC8739, we monitored the peritoneal cavity to detect and quantify the release and presence of several immune mediators (FIG. 4E). Mast-MO-treated groups exhibited a pronounced ability to induce leukocyte migration to the site of infection, a key step into resolving infections, compared to the mast-L-treated group (FIG. 4B). This effect was similar to the positive control group of mice treated with transglutaminase (TGA) (FIG. 4B). Whereas mast-L did not significantly induce leukocyte recruitment over the time period tested, mast-MO stimulated recruitment at all time points with a peak of ~10$^8$ observed 3 h post-infection (FIG. 4B). After 24 h, the leukocyte recruitment levels in mast-MO-treated mice dropped to ~10$^6$, likely attributed to the resolution of the infection by the peptide (FIGS. 5B and 5C). These results are consistent with the intrinsic ability of the pentapeptide motif FLPII to act as a chemoattractant (FIG. 1A), in line with our initial design, and highlight the immune boosting capability of our designed peptide. The concentration of interleukin-12 (IL-12), a protein produced mainly by macrophages and neutrophils in response to antigenic stimulation, and the pro-inflammatory cytokine tumor necrosis factor alpha (TNFα) were also longitudinally tracked for 48 h. Mast-MO and mast-L repressed both pro-inflammatory cytokines, in addition to IL-6, thus showing their ability to repress inflammation in vivo (FIG. 4C-4F). We monitored, via ELISAs, the cytokine profiles present within the peritoneal cavity of mice infected with *E. coli* ATCC8739 and *S. aureus* ATCC29213 (FIGS. 4E and FIG. 4F, respectively) and treated with a single dose of peptide. Treatment with peptides in both cases led to a significant decrease in the inflammatory response within the peritoneal fluid resulting from the bacterial infection, thus highlighting the potential of the peptides as anti-inflammatory agents. These results confirmed that mast-MO appeared to control inflammation in addition to acting as a chemoattractant for leukocytes. Overall, these data suggest that mast-MO helps balance host responses by reducing the prolonged production of pro-inflammatory mediators while enhancing the activity and recruitment of leukocytes, which are important for baseline immune function.

Figure 5H:
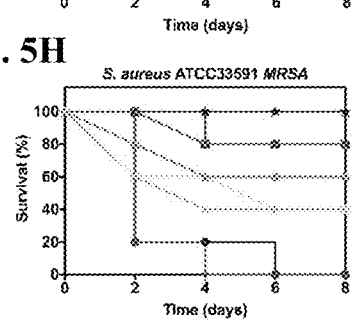
Figure 5I:
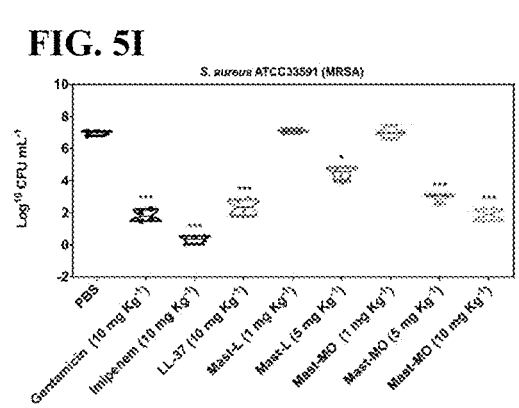

Synthetic peptide mast-MO confers protection to mice against lethal septicemia caused by bacterial infections. To determine the anti-infective activity of mast-MO in a pre-clinical mouse model, the ability of the peptide to kill pathogenic and drug-resistant *E. coli* and *S. aureus* strains was tested in a systemic sepsis infection mouse model (FIG. 5). The minimal bacterial load resulting in a lethal dose (LD$_{100}$) 24 h post-intraperitoneal injection was first determined. The following LD$_{100}$ were determined: ~2×10$^4$ for *E. coli* ATCC8739 and *E. coli* 1812446 and ~2×10$^9$ for *S. aureus* ATCC29213 and *S. aureus* (MRSA) ATCC33591. Mice were infected with the LD$_{100}$ of bacteria and treated 3 h post-infection with either mast-L (1 and 5 mg Kg$^{-1}$) or mast-MO (1, 5 and 10 mg Kg$^{-1}$), which were also administered intraperitoneally. Mice infected with *E. coli* ATCC8739 and clinical isolate *E. coli* 1812446 (KPC-positive) and subsequently treated with mast-L (5 mg Kg$^{-1}$) displayed decreased survival compared to groups treated with mast-MO (5 and 10 mg Kg$^{-1}$) (FIG. 5B-5C and FIG. 5F-5G, respectively). Overall, mice treated with mast-MO exhibited 80% survival whereas those treated with mast-L displayed 40 to 60% survival. Mouse groups treated with mast-L at 10 mg Kg$^{-1}$ had to be euthanized due to observed toxic effects when the peptide was injected systemically. Conversely, mice treated with mast-MO (10 mg Kg$^{-1}$) were completely protected from infection by *S. aureus* ATCC29213 (FIG. 5D-5E), while those treated with mast-L (5 mg Kg$^{-1}$) presented 80% survival. Finally, mice infected with *S. aureus* MRSA ATCC33591 and treated with mast-MO (10 mg Kg$^{-1}$) exhibited 80% survival (FIG. 5H-5I). Only 60% of mice infected with *S. aureus* MRSA ATCC33591 and treated with mastoparan-L (5 mg Kg$^{-1}$) survived. Once again, mice treated with 10 mg Kg$^{-1}$ of mast-L had to be euthanized.

In summary, in all systemic infection experiments performed, 10 mg Kg$^{-1}$ of mast-MO led to significant reduction of bacterial counts and high survival rates, comparable to standard-of-care antibiotics, such as the aminoglycoside gentamicin and the β-lactam imipenem, which are usually administered at 1-30 mg Kg$^{-1}$ in mouse models (33). These results further confirmed in vivo that mast-MO did not present toxicity in the mouse model tested, whereas the wasp venom peptide mast-L led to toxicity when injected systemically at 10 mg Kg$^{-1}$. Mast-MO, even at relatively low doses (10 mg Kg$^{-1}$), proved to be an excellent anti-infective agent, leading to complete inhibition of otherwise lethal bacterial infections caused by drug-resistant and clinically relevant Gram-negative and Gram-positive pathogens. The present in vivo data also demonstrated the dual activity of the presently disclosed engineered synthetic peptide mast-MO to both modulate the immune response and directly kill bacteria (FIG. 6A).

Example 3—Preparation and Assessment of Mast-MO Derivatives

In order to deplete the remaining toxicity observed in mast-MO towards certain human cells (e.g., HEK293; Table 2), the inventors designed and synthesized a permutation library of 59 novel mast-MO derivatives (Table 7) composed of single amino acid permutations of the FLPII motif (FIG. 6B).

TABLE 7

Amino acid sequences and aggregation in water of the mast-MO analogs and other peptides from the mastoparan family synthesized and tested in this work.

| Peptide | Sequence | Agg. |
|---|---|---|
| Galparan (SEQ ID NO: 2) | GWTLNSAGYLLGPINLKALAALAKKIL | NO |
| Transportan (SEQ ID NO: 3) | GWTLNSAGYLLGKINLKALAALAKKIL | NO |
| TP10 (SEQ ID NO: 4) | AGYLLGKINLKALAALAKKIL | NO |
| Mast-MO (SEQ ID NO: 5) | FLPIIINLKALAALAKKIL | NO |
| 1 (SEQ ID NO: 6) | LFIIPINLKALAALAKKIL | NO |
| 2 (SEQ ID NO: 7) | IFLPIINLKALAALAKKIL | NO |
| 3 (SEQ ID NO: 8) | IIPFLINLKALAALAKKIL | NO |
| 4 (SEQ ID NO: 9) | LIPFIINLKALAALAKKIL | NO |
| 5 (SEQ ID NO: 10) | LIPIFINLKALAALAKKIL | NO |
| 6 (SEQ ID NO: 11) | LPIIFINLKALAALAKKIL | NO |
| 7 (SEQ ID NO: 12) | IIPLFINLKALAALAKKIL | NO |
| 8 (SEQ ID NO: 13) | ILIFPINLKALAALAKKIL | NO |
| 9 (SEQ ID NO: 14) | PLIFIINLKALAALAKKIL | ++ |
| 10 (SEQ ID NO: 15) | PLIIFINLKALAALAKKIL | + |
| 11 (SEQ ID NO: 16) | PILFIINLKALAALAKKIL | + |
| 12 (SEQ ID NO: 17) | IPFILINLKALAALAKKIL | NO |
| 13 (SEQ ID NO: 18) | IPLFIINLKALAALAKKIL | NO |
| 14 (SEQ ID NO: 19) | LFIIPINLKALAALAKKIL | NO |
| 15 (SEQ ID NO: 20) | IFLPIINLKALAALAKKIL | NO |
| 16 (SEQ ID NO: 21) | IIPFLINLKALAALAKKIL | NO |
| 17 (SEQ ID NO: 22) | LIPFIINLKALAALAKKIL | NO |
| 18 (SEQ ID NO: 23) | ILFIPINLKALAALAKKIL | ++ |
| 19 (SEQ ID NO: 24) | IFLIPINLKALAALAKKIL | NO |
| 20 (SEQ ID NO: 25) | LIFIPINLKALAALAKKIL | NO |
| 21 (SEQ ID NO: 26) | ILFPIINLKALAALAKKIL | NO |
| 22 (SEQ ID NO: 27) | PFLIIINLKALAALAKKIL | + |
| 23 (SEQ ID NO: 28) | FILIPINLKALAALAKKIL | NO |
| 24 (SEQ ID NO: 29) | IFPLIINLKALAALAKKIL | NO |
| 25 (SEQ ID NO: 30) | LIIPFINLKALAALAKKIL | NO |
| 26 (SEQ ID NO: 31) | PIILFINLKALAALAKKIL | NO |
| 27 (SEQ ID NO: 32) | FIPLIINLKALAALAKKIL | NO |
| 28 (SEQ ID NO: 33) | IPFLIINLKALAALAKKIL | NO |
| 29 (SEQ ID NO: 34) | IIFLPINLKALAALAKKIL | ++ |
| 30 (SEQ ID NO: 35) | LIIFPINLKALAALAKKIL | NO |
| 31 (SEQ ID NO: 36) | LFPIIINLKALAALAKKIL | NO |
| 32 (SEQ ID NO: 37) | FLIPIINLKALAALAKKIL | NO |
| 33 (SEQ ID NO: 38) | PFIILINLKALAALAKKIL | NO |
| 34 (SEQ ID NO: 39) | IFIPLINLKALAALAKKIL | NO |
| 35 (SEQ ID NO: 40) | FILPIINLKALAALAKKIL | NO |
| 36 (SEQ ID NO: 41) | IILFPINLKALAALAKKIL | NO |
| 37 (SEQ ID NO: 42) | PLFIINLKALAALAKKIL | NO |
| 38 (SEQ ID NO: 43) | FIPILINLKALAALAKKIL | NO |
| 39 (SEQ ID NO: 44) | IFPILINLKALAALAKKIL | NO |
| 40 (SEQ ID NO: 45) | IPILFINLKALAALAKKIL | NO |
| 41 (SEQ ID NO: 46) | ILIPFINLKALAALAKKIL | + |
| 42 (SEQ ID NO: 47) | IFILPINLKALAALAKKIL | NO |
| 43 (SEQ ID NO: 48) | IPIFLINLKALAALAKKIL | NO |
| 44 (SEQ ID NO: 49) | IILPFINLKALAALAKKIL | ++ |
| 45 (SEQ ID NO: 50) | IPLIFINLKALAALAKKIL | NO |
| 46 (SEQ ID NO: 51) | FIILPINLKALAALAKKIL | NO |
| 47 (SEQ ID NO: 52) | FLIIPINLKALAALAKKIL | NO |
| 48 (SEQ ID NO: 53) | PIFILINLKALAALAKKIL | + |
| 49 (SEQ ID NO: 54) | FPIILINLKALAALAKKIL | NO |
| 50 (SEQ ID NO: 55) | FIIPLINLKALAALAKKIL | NO |
| 51 (SEQ ID NO: 56) | PIFLIINLKALAALAKKIL | NO |
| 52 (SEQ ID NO: 57) | FPLIIINLKALAALAKKIL | NO |
| 53 (SEQ ID NO: 58) | LPIFIINLKALAALAKKIL | ++ |
| 54 (SEQ ID NO: 59) | PIIFLINLKALAALAKKIL | NO |
| 55 (SEQ ID NO: 60) | LFIPIINLKALAALAKKIL | NO |
| 56 (SEQ ID NO: 61) | ILPIFINLKALAALAKKIL | ++ |
| 57 (SEQ ID NO: 62) | PILIFINLKALAALAKKIL | NO |
| 58 (SEQ ID NO: 63) | FPILIINLKALAALAKKIL | NO |
| 59 (SEQ ID NO: 64) | LIFPIINLKALAALAKKIL | ++ |

Figure 10:
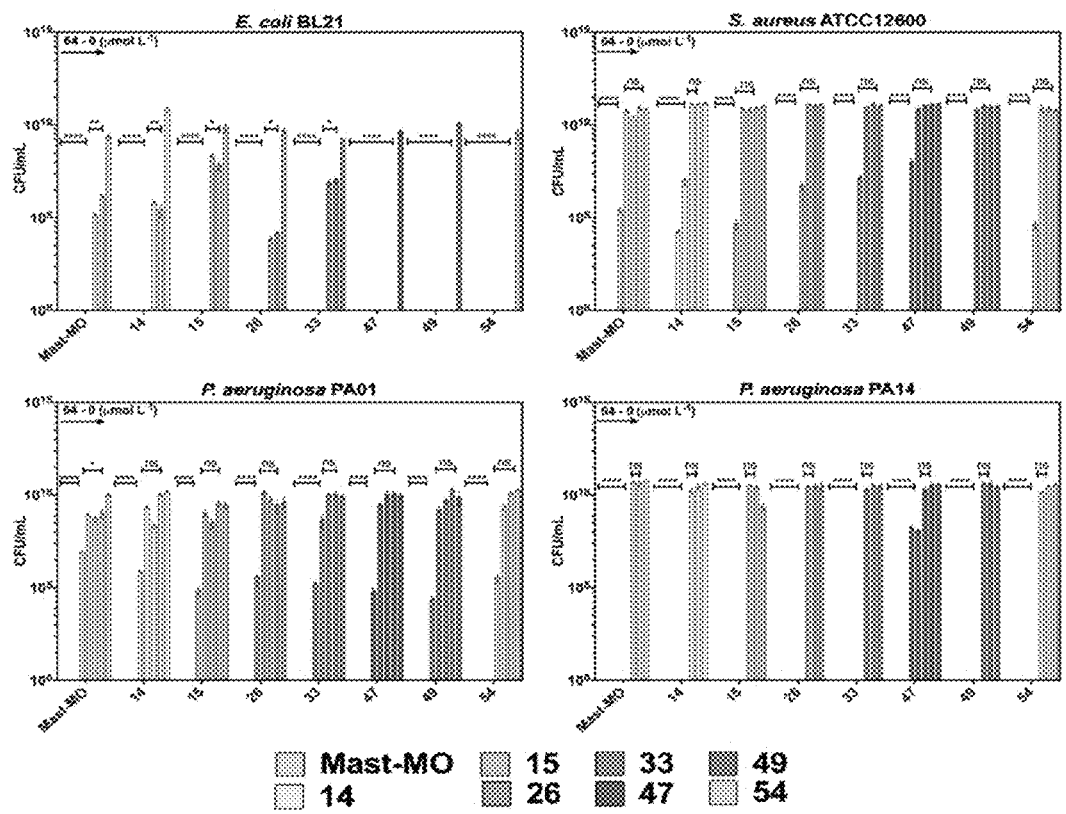
FIG. 10 depicts colony forming units (CFU) count assays to quantify the antimicrobial activity of mast-MO and its synthetic analogs. Briefly, $10^5$ bacterial cells and serially diluted (0-64 μmo$L^{-1}$) peptides were added to a 96-well plate and incubated at 37° C. One day after exposing bacteria to the peptides, the solution in each well was 10-fold diluted seven times and the serial dilutions were plated in agar plates, which were incubated for 22 h at 37° C. (B) Next, bacterial colonies were counted. All assays were performed in three biological replicates (statistical significance was determined using two-way ANOVA followed by Dunnett's test, error bars=standard error of the mean, ns=statistically not significant, *p<0.05, p<0.005, *p<0.001, ****p<0.0001).

The FLPII motif was chosen for the permutations to preserve the natural antimicrobial activity of mast-L and also conserve the hydrophobic content inserted in the N-terminal extremity for the initial design of mast-MO. Next, we assessed the antimicrobial (FIG. 10) and cytotoxic activities of the mast-MO analog library against HEK293 cells (FIG. 6C). These specific cell line was chosen as it derives from human embryonic kidney cells and potential antimicrobial (i.e., AMPs, antibiotics) toxicity affects the kidneys, which are responsible for clearing such molecules (34). Also measured was whether the peptides aggregated at the highest concentration tested (128 μmoL$^{-1}$) (Table 7) since the motif inserted is composed of residues with aliphatic or aromatic side chain groups that may be prone to aggregation when in proximity within the primary peptide sequence, thus altering biological activity. Minor changes to the first five residues inserted in the mast-MO primary sequence led to a pronounced decrease in cytotoxic activity (2.5 to 5-fold) compared to mast-MO (FIG. 6C).

The most active peptides obtained, which were not cytotoxic and did not aggregate in aqueous solution, were selected and tested in a skin scarification mouse model that mimics an epithelial abscess infection (7, 12, 35). Mice were infected topically with the Gram-negative pathogen *P. aeruginosa* and subsequently treated with a single low dose (16 µmol $L^{-1}$) of the seven lead synthetic peptides (analogs 14, 15, 26, 33, 47, 49, and 54—FIG. 6D-6F and Table 6). The peptides did not cause any side effects or adverse toxicity (i.e., hemolysis or cytotoxicity) towards mouse or human cell lines (FIG. 6E). Synthetic analogs (IFLPIINL-KALAALAKKIL-NH2) (SEQ ID NO: 20) and 49 (FPIILINLKALAALAKKIL-NH2) (SEQ ID NO: 54) displayed increased anti-infective activity compared to their parent peptide mast-MO (FIG. 6E). Analog 15 is very similar to mast-MO as the permutation used to generate this molecule involved insertion an Ile residue at the beginning of the sequence while maintaining the last four residues of mast-MO. On the other hand, analog 49 presented all its aliphatic residues next to each other in positions three to five of the added motif, contrary to mast-MO that has a leucine residue in position two. Overall, several bactericidal mast-MO analogs were designed by permuting the 5 amino acid residues that compose the FLPII and 2 of these analogs presented high anti-infective activity with a single dosage in a skin abscess formation mouse model at low micromolar concentration (16 µmol $L^{-1}$), comparable to the most active anti-infective peptides (7, 12).

Materials and Methods

Peptide synthesis. Mast-L, mast-MO and LL-37 were purchased from Shanghai Hanhong Chemical (China) and Mast-MO analogs were purchased from Biopolymers (MIT). The peptides were synthesized using the solid-phase peptide synthesis and N-9-fluoromethyloxycarbonyl (Fmoc) strategy and purified by high-performance liquid chromatography (HPLC). Peptide purity used in biologic assays was higher than 95%.

Circular Dichroism spectroscopy. The circular dichroism (CD) experiments were performed to determine the ideal conditions for carrying out the NMR experiments, including conformational preferences and the stability ratio at different pH and media concentrations. Mast-L at 70 µmol$L^{-1}$ and mast-MO at 50 µmol$L^{-1}$ were analyzed in SDS (100 mmol $L^{-1}$), DPC (15 mmol $L^{-1}$), TFE/Water (1:1, v:v), and PCPG (1 mmol $L^{-1}$) phospholipid vesicles, at 20° C. The spectra were recorded on a Jasco J-815 spectropolarimeter coupled to a Peltier Jasco PTC-423L (Tokyo, Japan), using a 1.0 mm path length rectangular quartz cuvette (NSG, Farmingdale NY), six accumulations from 260 to 190 nm, 1.0 nm spectral bandwidth, 0.2 nm step resolution, 100 nm $min^{-1}$ scan speed and 1 s response time. Similar experiments with the respective blank solutions were performed for background subtraction. The spectra were analyzed using the CDPro software package (36, 37). The relative helix content ($f_H$) was calculated from the ellipticity values at 222 nm as described by Chen et al. (38)

NMR spectroscopy and structure calculations. The samples were prepared by dissolving the peptide stock solution (1 mmol $L^{-1}$) in 500 µL $H_2O/D_2O$ (9/1, v/v) in a micellar solution containing 100 mmol $L^{-1}$ of sodium dodecyl sulfate (SDS-$d_{25}$), pH 4.0 and 25° C. All spectra were recorded on a Bruker Avance III 500 spectrometer equipped with a 5 mm broadband inverse (BBI) probehead. Proton chemical shifts were referenced to trimethylsilyl-2,2,3,3-$d_4$-propionate sodium (TMSP-$d_4$).

$^1H$-$^1H$ TOCSY experiments were recorded with 40 transients of 4096 data points, 512 t1 increments and spinlock mixing time of 80 ms. $^1H$-$^1H$ NOESY spectra were recorded with 64 transients of 1024 data points, 512 t1 increments and mixing time of 100, 150, 200 and 250 ms. $^1H$-$^{13}C$ HSQC experiments, edited mode, were acquired with spectral widths F1 of 20831 and F2 of 8012 Hz, and 80 transients of 4096 points for each free induction decay and 256 t1 increments were used. $^1H$-$^{15}N$ sf-HMQC (Heteronuclear multiple-quantum coherence) experiments were recorded with 1024 data points and 80 t1 increments, 7,600 transients for mastoparan-L and 7,000 for mastoparan-MO. All 2D-NMR data were processed using NMRPIPE (39) and analyzed with NMRView (40) software.

The $^1H$-$^1H$ NOESY spectra revealed a total of 219 distance restraints for mast-L and 221 for mast-MO, with 15.6 and 11.6 average restrictions per residue, respectively. The ten structures obtained for each of the mastoparan peptides were highly convergent, i.e. mast-MO is a well-structured helical peptide. We also observed that when each one of the peptides had their structured region aligned, they presented RMSD values of 0.47±0.15 Å and 0.41±0.18 Å, for mast-L and mast-MO respectively. Despite the random character of the N-terminal region, the RMSD of all aligned amino acid residues was 0.76±0.25 and 0.98±0.30 Å (mean±standard deviation of nine samples), for mast-L and mast-MO, respectively. This indicates a geometric distribution and conformational flexibility of both mastoparans. The average of the ten Ramachandran plots for mast-L shows that 94.2% of the φ and ψ angles are in most favored α-helical regions and 5.8% in allowed regions, whereas mast-MO exhibits 100% of the φ and Ψ angles in the most favored α-helical regions (http://mordred.bioc.cam.ac.uk/—rapper/rampage.php). These results indicated that the calculated structures were predicted accurately. Additionally, we checked the fold accuracy using ProSA II (41), which indicated Z-score values of −6.00 and −3.56 for mast-MO and mast-L, respectively. These values indicated the absence of erroneous parts of our models, which points to the accuracy of the structure prediction.

$H_2O/D_2O$ exchange kinetics experiments were performed using a solution of 1 mM of the peptide in the presence of 100 mmol $L^{-1}$ of SDS-$d_{25}$ diluted in $H_2O/D_2O$ (1:9, v/v) to a final volume of 600 µL. TMSP-$d_4$ was used as the reference standard. Thirty minutes were spent between the preparation of the sample and the beginning of the data collection. TOCSY experiments were performed every 2 h at the temperature of 298 K for 7 day.

The structure calculations and refinement were performed using the program XPLOR-NIH version 2.28 by simulated annealing (SA) algorithm (42). NOE cross peak volumes were converted into semi-quantitative distance restraints using the calibration by Hyberts et al. (43). The upper limits of the distances restrain obtained were calibrated for 2.8, 3.4, and 5.0 Å, being strong, medium, and weak NOE, respectively. Once attributed the NOE correlations and the chemical shifts of the backbone atoms in the respective contour maps, these were respectively converted into distance and dihedral angle restrains, which were employed in simulated annealing calculations to generate the structures of the mastoparan peptides. Both phi (φ) and psi (ψ)

backbone dihedral angles were predicted, by analysis of $^1H_\alpha$ and $^{13}C_\alpha$, using TALOS+(44). Starting with an extended conformation, 200 structures were calculated, 20 structures were selected, from the 200 calculated structures, and refined in water (42). The 10 lowest energy conformations were selected.

Protein Structure Validation Suite (PSVS 5.2 server) was used to evaluate the quality of the structures (http://psys-1_5-dev.nesg.org/). The stereochemical quality of the lowest energy structures, was evaluated using PROCHECK through the Ramachandran plot (http://mordred.bioc.cam.a-c.uk/—rapper/rampage.php) and ProSA (Protein Structure Analysis) indicated the fold quality Z-scores. The display, analysis, manipulation of the molecular graphics images and root mean square deviation (RMSD) calculations were performed using either PyMOL (The PyMOL Molecular Graphics System, http://www.pymol.org) and MOLMOL (45) software.

Bacterial strains and media. Strains used included clinical isolates *Escherichia coli* KPC-positive ID No. 1812446, *Escherichia coli* multidrug-resistant ID 2101123 and carbapenemase-producing *Klebsiella pneumoniae* KPC-positive ID 1825971, as well as reference strains *Bacillus subtilis* ATCC6633, *Enterococcus faecalis* ATCC12953, *Staphylococcus aureus* ATCC29213, Methicillin-Resistant *Staphylococcus aureus* ATCC33591, *Streptococcus pyogenes* ATCC19615, *Escherichia coli* ATCC8739, *Klebsiella pneumoniae* ATCC13885, *Proteus mirabilis* ATCC25933, *Pseudomonas aeruginosa* ATCC 15442, *Salmonella enterica* ATCC14028, *Acinetobacter baumannii* ATCC19606, *Escherichia coli* ATCC11775, *Escherichia coli* AIG221, *Escherichia coli* AIG222, *Escherichia coli* BL21, *Klebsiella pneumoniae* ATCC133883, *Pseudomonas aeruginosa* PAO1, *Pseudomonas aeruginosa* PA14 and *Salmonella enterica* RFP. Bacteria were plated on brain heart infusion broth (BHI) (Himedia, India) from a frozen stock. Following 24 h of incubation of the agar plate, three isolated colonies were transferred to 1 mL of BHI. The broth culture was incubated overnight (12-16 h) at 37° C. with shaking.

Antibacterial assays. Minimum inhibitory concentration (MIC) of peptides and antibiotics were evaluated using the broth microdilution technique in Mueller-Hinton Broth medium (MHB) with an initial inoculum of $5\times10^5$ cells in nontreated Polystyrene microtiter plates (Corning, USA) in accordance with Wiegand et al. The MIC was interpreted as the lowest concentration of peptide or antibiotic that completely inhibited the visible growth of bacteria after 12 h of incubation of the plates at 37° C. Each agent was tested in triplicate in at least three independent experiments. The MIC assays were also performed using the broth microdilution method in sterile 96-well polypropylene microtiter plates. Peptides were added to the plate as solutions in BM2 minimal medium in concentrations ranging from 0 to 128 μg·mL$^{-1}$, and the bacteria (*E. coli* BL21, *S. aureus* ATCC12600, *P. aeruginosa* PA01 and PA14) were grown overnight at 37° C. and inoculated at a final concentration of $5\times10^5$ CFU mL$^{-1}$ per well. The plates were incubated at 37° C. for 24 h and read in a plate reader at 610 nm. All assays were done in triplicate.

Bacterial killing assays. The bacterial killing experiments involved performing 1:100 dilutions of overnight cultures of *E. coli* BL21, *S. aureus* ATCC12600, *P. aeruginosa* PAO1 and PA14 in the absence or presence of increasing concentrations of the samples (0-200 μg mL$^{-1}$). After 24 h of treatment, 10-fold serial dilutions were performed, bacteria were plated on LB agar plates (*E. coli* BL21 and *S. aureus* ATCC12600) and *Pseudomonas* Isolation Agar (*P. aeruginosa* PAO1 and PA14) and allowed to grow overnight at 37° C. after which colony forming unit (CFU) counts were recorded. All experiments were done in triplicates.

Antibiofilm assays. Experiments were performed as described previously. Biofilms were grown in BM2 glucose medium for 72 h, at 37° C. in flow cell chambers with channel dimensions of $1\times4\times40$ mm, as previously described by de la Fuente-Nunez et al. For the treatment of pre-formed biofilms, bacteria were allowed to develop structured 2-day-old biofilms prior to treatment with peptides for the following 24 h. Biofilm cells were then stained using the Live/Dead BacLight bacterial viability kit (Molecular Probes, Eugene, OR) and subsequently examined using a confocal laser scanning microscope (Olympus, Fluoview FV1000); three-dimensional reconstructions were generated using the Imaris software package (Bitplane AG).

Hemolysis assays. Hemolytic activity of peptides was determined by using fresh mouse red blood cells (mRBCs), by measuring the peptide-induced changes of the optical density (OD) at 540 nm (Victor X, Perkin-Elmer, Germany), 100% lysis was determined by analysing the supernatant of erythrocytes that had been incubated with Triton X-100 (1%).

Mammalian cells toxicity assays. L929 mice fibroblasts (Rio de Janeiro Cell Bank) and SPCs were seeded in 96-well microtiter plates in a concentration of $1.0\times10^5$ cells per well, in DMEM medium, supplemented with different concentrations of tested peptides (1-600 μM). After 48 h incubation, a thiazolyl blue tetrazolium bromide (MTT) protocol was performed. Briefly, 60% of the medium was removed, and 10 μL of MTT (5 mg mL$^{-1}$) (Sigma, USA) solution was added to each well and the plate was incubated for 4 h, in 5% $CO_2$, at 37° C. The blue formazan product generated was dissolved by the addition of 100 μL of 100% DMSO (Mallinckrodt, Germany) per well. Plates were then gently swirled for 5 min, at room temperature, to dissolve the precipitate. The absorbance was monitored at 575 nm using a microplate spectrophotometer (Bio-Tek, USA). Cytotoxicity was determined as a percentage of the maximum value after subtracting the background. The results were expressed as the percentage of each sample compared to the negative control (PBS buffer, pH 7.4) and cell culture was incubated in a lysis buffer (10 mM Tris, pH 7.4, 1 mM ethylenediamine tetraacetic acid (EDTA), and 0.1% Triton X-100).

Membrane permeabilization assays. The membrane permeability of the mast-MO (20 μmol L$^{-1}$) was determined by using the N-phenyl-1-napthylamine (NPN) uptake assay. All the bacterial strains were grown to $OD_{600}$ of 0.4, centrifuged (10,000 rpm at 4° C. for 10 min), washed and resuspended in buffer (5 mmol L$^{-1}$ HEPES, 5 mmol L$^{-1}$ glucose, pH 7.4). 4 μL of NPN solution (0.5 mmol L$^{-1}$—working concentration of 10 μmol L$^{-1}$ after dilutions) was added to 100 μL of the bacterial solution in a white 96-wells plate. The background fluorescence was recorded at $\lambda_{ex}=350$ nm and $\lambda_{em}=420$ nm. Mast-MO samples in water (100 μL solution at 1.2 μmol L$^{-1}$) were added to the 96-wells plate, and fluorescence was recorded as a function of time until no further increase in fluorescence was observed (20 min).

Membrane depolarization assays. The cytoplasmic membrane depolarization activity of mast-MO (20 μmol L$^{-1}$) was determined by the membrane potential—sensitive dye, $DiSC_3(5)$. Briefly, the bacterial strains were grown at 37° C. with agitation to the mid-log phase ($OD_{600}=0.5$). The cells were centrifuged and washed twice with washing buffer (20 mmol L$^{-1}$ glucose, 5 mmol L$^{-1}$ HEPES, pH 7.2) and resuspended to an $OD_{600}$ of 0.05 in the same buffer (20 mmol L$^{-1}$ glucose, 5 mmol L$^{-1}$ HEPES, pH 7.2) but containing 0.1 mol $L^{-1}$ KCl. Thereafter, the cells (100 µL) were incubated for 15 min with 20 nmol $L^{-1}$ of $DiSC_3(5)$ until a stable reduction of fluorescence was achieved, indicating the incorporation of the dye into the bacterial membrane. Membrane depolarization was then monitored by observing the change in the fluorescence emission intensity of the membrane potential—sensitive dye, $DiSC_3(5)$ ($\lambda_{ex}$=622 nm, $\lambda_{em}$=670 nm).

Bacterial toxicity mouse model. Six-weeks-old female C57BL/6 mice were used in the murine systemic infection model. Animals were provided by the Central Bioterium of the Universidade de Sao Paulo-Ribeirão Preto. All animals were housed in individual cages under a constant temperature (22° C.) and humidity with a 12 h light/dark cycle and had access to food and water ad libitum throughout the study. The mice were euthanized by $CO_2$ at the end of the experiments. All procedures, care, and handling of the animals were approved by the Ethics Committee of the Catholic University of Brasilia number 005/13. CD-1 IGS female mice (6-weeks-old) were used for the skin scarification model and maintained in accordance with the Guide for the Care and Use of Laboratory Animals in an AAALAC-accredited facility.

Systemic bacterial infection mouse model. Acute toxicity assay was performed based on the work of Navon-Venezia and co-workers (46). The experiment was performed by intraperitoneal (i.p.) injection of the tested peptides to groups of 10 C57BL/6 mice. Each mouse was injected with a 0.5 mL solution of freshly prepared of peptides in PBS. The doses of peptide administered per mouse were 0, 10, 30, 50, 70 and 90 mg $Kg^{-1}$ of body weight. Animals were directly inspected for adverse effects for 6 h, and mortality was monitored for 7 days thereafter. Differences between groups were analysed using the Fisher exact test (differences were considered to be statistically significant when the P value was <0.05). Briefly, E. coli ATCC8739 and E. coli 1812446 or S. aureus ATCC 29213 and S. aureus (MRSA) ATCC33591 were plated on tryptic soy agar plus 5% sheep blood (blood agar, Himedia, India) from a frozen stock. Following 24 h of incubation of the agar plate, three isolated colonies were transferred to 1 mL of BHI. The broth culture was incubated overnight (12-16 h) at 37° C. with shaking. Based on preliminary experiments to determine the challenge dose of E. coli ATCC8739 and E. coli KPC-positive ID 1812446 or S. aureus ATCC29213 and S. aureus (MRSA) ATCC33591 that resulted in consistent systemic infection without rapidly killing the mice, the broth-grown bacteria were diluted to ~$2\times10^4$ (CFU/mL per mouse in phosphate buffered saline—PBS) for Gram-negative bacteria and $2\times10^9$ (CFU/mL per mouse in PBS) for Gram-positive bacteria. Mice were challenged with either strain of E. coli ATCC8739 and E. coli 1812446 or S. aureus ATC29213 and S. aureus (MRSA) ATCC33591 in a final volume of 200 µL of PBS by intraperitoneal injection (i.p.). The day of challenge was designated as day 1 of the experiment. Three hours after bacterial injection, mice (n=5) were treated, intraperitoneally, with different concentrations of peptides (1, 5 or 10 mg $Kg^{-1}$), LL-37, gentamicin and 10 mg $Kg^{-1}$ of imipenem or PBS for 8 days. For bacterial load evaluation, 5 mice per group were used. Animals were humanely killed 24 h after bacterial administration. To detect bacterial colonization, the peritoneal lavage samples were collected under sterile conditions. The peritoneal lavage was obtained by washing the cavity with 5 mL of sterile PBS. Samples were diluted serially, and 100 µL of each dilution was spread in duplicate on appropriate agar plates for the count of developed colonies. Cytokine levels (i.e., IFN-γ, IL-6, IL-10, IL-12p70 and TNF-α) in the peritoneal lavage of the mice both in the absence and presence of peptide treatment were quantified by ELISA (Peprotech, USA) according to the manufacturer's instructions.

Isolation of leukocytes from the peritoneal cavity of mice. Leukocyte migration into the peritoneal cavity of uninfected C57BL/6 mice treated with 10 mg $Kg^{-1}$ of peptides was evaluated to assess the chemotactic activity of the peptides, as previously described (11). Specifically, 10 mg $Kg^{-1}$ of peptides suspended in sterile saline were injected i.p. in C57BL/6 mice. Mice were subsequently euthanized, and their peritoneal lavage was collected over time. Leukocyte counts present in the in peritoneal cavity of mice infected with E. coli ATCC 8739 were quantified. Animals infected and treated with peptides were euthanized over time (0.5-24 h) post-treatment, and a peritoneal lavage was carried out to quantify leukocyte numbers present in the peritoneal cavity (47). Thioglycolate (TGA) 3% was used as a positive control for leukocyte migration. Animals were sacrificed, and cells present in the peritoneal cavity were harvested in 3 mL of PBS containing 1 mmol $L^{-1}$ EDTA. Total cell counts were quantified using a cell counter (Coulter AC T series analyzer), and differential cell counts were conducted on cytocentrifuge slides (Cytospin 3; Thermo Shandon) stained by the May-Grünwald-Giemsa (Rosenfeld) method. The results are expressed as the number of cells per cavity (48).

Skin abscess infection mouse model. P. aeruginosa strain PAO1 was used for inducing a skin infection in the mouse model as described by Pane et al. (9). Briefly, bacteria were grown in tryptic soy broth medium. Subsequently, cells were washed twice with sterile PBS (pH 7.4, 13,000 rpm for 1 min), and resuspended to a final concentration of $1\times10^7$ CFU/20 µL. Female CD-1 mice (six-weeks old) were anesthetized with isoflurane and had their backs shaved and a superficial linear skin abrasion was made with a needle in order to damage the stratum corneum and upper-layer of the epidermis. An aliquot of 20 containing $1\times10^7$ CFU of bacteria in PBS was inoculated over each defined area containing the scratch with a pipette tip. One day after the infection, peptides (16 µmol $L^{-1}$) were administered to the infected area. Animals were euthanized and the area of scarified skin was excised two- and four-days post-infection, homogenized using a bead beater for 20 minutes (25 Hz), and serially diluted for CFU quantification. Two independent experiments were performed with 3 mice per group in each condition (n=6 per group).

REFERENCES

The following publications may also be relevant to the present disclosure:
1. de la Fuente-Nunez C, Torres M D, Mojica F J, Lu T K (2017) Next-generation precision antimicrobials: towards personalized treatment of infectious diseases. *Curr Opin Microbiol* 37:95-102.
2. Centers for Disease Control and Prevention (2019) 2019 *Antimicrobial Resistant Threats Report* Available at: https://www.cdc.gov/drugresistance/biggest-threats.html.
3. Rudd K E, et al. (2020) Global, regional, and national sepsis incidence and mortality, 1990-2017: analysis for the Global Burden of Disease Study. *Lancet* 395(10219): 200-211.
4. Morens D M, Taubenberger J K, Fauci A S (2008) Predominant Role of Bacterial Pneumonia as a Cause of Death in Pandemic Influenza: Implications for Pandemic Influenza Preparedness. *J Infect Dis* 198(7):962-970.

5. Zhou F, et al. (2020) Clinical course and risk factors for mortality of adult inpatients with COVID-19 in Wuhan, China: a retrospective cohort study. *Lancet* 395(10229):1054-1062.
6. Lewis R J, Garcia M L (2003) Therapeutic potential of venom peptides. *Nat Rev Drug Discov* 2(10):790-802.
7. Torres M D T, et al. (2018) Structure-function-guided exploration of the antimicrobial peptide polybia-CP identifies activity determinants and generates synthetic therapeutic candidates. *Commun Biol* 1:221.
8. Torres M D T, Sothiselvam S, Lu T K, de la Fuente-Nunez C (2019) Peptide Design Principles for Antimicrobial Applications. *J Mol Biol*:In Press.
9. Cardoso M H, et al. (2018) A Computationally Designed Peptide Derived from *Escherichia coli* as a Potential Drug Template for Antibacterial and Antibiofilm Therapies. *ACS Infect Dis* 4(12):1727-1736.
10. Candido E S, et al. (2019) Short Cationic Peptide Derived from Archaea with Dual Antibacterial Properties and Anti-Infective Potential. *ACS Infect Dis*. doi:10.1021/acsinfecdis.9b00073.
11. Silva O N, et al. (2016) An anti-infective synthetic peptide with dual antimicrobial and immunomodulatory activities. *Sci Rep* 6(1):35465.
12. Porto W F, et al. (2018) In silico optimization of a guava antimicrobial peptide enables combinatorial exploration for peptide design. *Nat Commun* 9(1):1490.
13. Oshiro K G N, et al. (2019) *Computer-Aided Design of Mastoparan-like Peptides* Enables the Generation of Nontoxic Variants with Extended Antibacterial Properties. *J Med Chem* 62(17):8140-8151.
14. Torres M D T, et al. (2017) Decoralin Analogs with Increased Resistance to Degradation and Lower Hemolytic Activity. *ChemistrySelect* 2(1):18-23.
15. Nijnik A, Hancock R (2009) Host defence peptides: antimicrobial and immunomodulatory activity and potential applications for tackling antibiotic-resistant infections. *Emerg Health Threats J* 2. doi:10.3134/ehtj.0.09.001.
16. Lima S M F, et al. (2017) Antimicrobial and immunomodulatory activity of host defense peptides, clavanins and LL-37, in vitro: An endodontic perspective. *Peptides* 95:16-24.
17. Kim W H, Lillehoj H S, Min W (2017) Evaluation of the Immunomodulatory Activity of the Chicken N K-Lysin-Derived Peptide cNK-2. *Sci Rep* 7(1):45099.
18. Lázár V, et al. (2018) Antibiotic-resistant bacteria show widespread collateral sensitivity to antimicrobial peptides. *Nat Microbiol* 3(6):718-731.
19. Higashijima T, Uzu S, Nakajima T, Ross E M (1988) Mastoparan, a peptide toxin from wasp venom, mimics receptors by activating GTP-binding regulatory proteins (G proteins). *J Biol Chem* 263(14):6491-4.
20. Mousli M, et al. (1989) Activation of rat peritoneal mast cells by substance P and mastoparan. *J Pharmacol Exp Ther* 250(1):329-35.
21. Higashijima T, Burnier J, Ross E M (1990) Regulation of Gi and Go by mastoparan, related amphiphilic peptides, and hydrophobic amines. Mechanism and structural determinants of activity. *J Biol Chem* 265(24):14176-86.
22. Wang G, Li X, Wang Z (2016) APD3: the antimicrobial peptide database as a tool for research and education. *Nucleic Acids Res* 44(D1):D1087—D1093.
23. Conlon J M, et al. (2009) Peptides with potent cytolytic activity from the skin secretions of the North American leopard frogs, Lithobates blairi and Lithobates yavapaiensis. *Toxicon* 53(7-8):699-705.
24. Goraya J, et al. (2000) Peptides with antimicrobial activity from four different families isolated from the skins of the North American frogs Rana luteiventris, Rana berlandieri and Rana pipiens. *Eur J Biochem* 267(3):894-900.
25. Yang X, Wang Y, Lee W-H, Zhang Y (2013) Antimicrobial peptides from the venom gland of the social wasp Vespa tropica. *Toxicon* 74:151-157.
26. Hernández-Gras F, Boronat A (2015) A hydrophobic proline-rich motif is involved in the intracellular targeting of temperature-induced lipocalin. *Plant Mol Biol* 88(3):301-311.
27. Bárány-Wallje E, Gaur J, Lundberg P, Lange Ü, Gräslund A (2007) Differential membrane perturbation caused by the cell penetrating peptide Tp10 depending on attached cargo. *FEBS Lett* 581(13):2389-2393.
28. Greenfield N J (2006) Using circular dichroism spectra to estimate protein secondary structure. *Nat Protoc* 1(6):2876-2890.
29. Wüthrich K (1986) *NMR of Proteins and Nucleic Acids* ed Sons J W (New York).
30. Irazazabal L N, et al. (2016) Selective amino acid substitution reduces cytotoxicity of the antimicrobial peptide mastoparan. *Biochim Biophys Acta-Biomembr* 1858(11):2699-2708.
31. Souza B M de, et al. (2015) Structure—activity relationship of mastoparan analogs: Effects of the number and positioning of Lys residues on secondary structure, interaction with membrane-mimetic systems and biological activity. *Peptides* 72:164-174.
32. Chen X, et al. (2018) Evaluation of the bioactivity of a mastoparan peptide from wasp venom and of its analogues designed through targeted engineering. *Int J Biol Sci* 14(6):599-607.
33. Pletzer D, Mansour S C, Wuerth K, Rahanj am N, Hancock R E W (2017) New Mouse Model for Chronic Infections by Gram-Negative Bacteria Enabling the Study of Anti-Infective Efficacy and Host-Microbe Interactions. *MBio* 8(1):e00140-17.
34. Brouwer CPJM, Wulferink M, Welling M M (2008) The Pharmacology of Radiolabeled Cationic Antimicrobial Peptides. *J Pharm Sci* 97(5):1633-1651.
35. Pane K, et al. (2018) Identification of Novel Cryptic Multifunctional Antimicrobial Peptides from the Human Stomach Enabled by a Computational—Experimental Platform. *ACS Synth Biol* 7(9):2105-2115.
36. Sreerama N, Woody R W (2000) Estimation of protein secondary structure from circular dichroism spectra: Comparison of CONTIN, SELCON, and CDSSTR methods with an expanded reference set. *Anal Biochem* 287(2):252-260.
37. Woody R W (2004) On the analysis of membrane protein circular dichroism spectra. *Protein Sci* 13:100-112.
38. Chen Y H, Yang J T, Chau K H (1974) Determination of the helix and beta form of proteins in aqueous solution by circular dichroism. *Biochemistry* 13(16):3350-9.
39. Delaglio F, et al. (1995) NMRPipe: a multidimensional spectral processing system based on UNIX pipes. *J Biomol NMR* 6(3):277-93.
40. Johnson B A, Blevins R A (1994) NMR View: A computer program for the visualization and analysis of NMR data. *J Biomol NMR* 4(5):603-14.
41. Wiederstein M, Sippl M J (2007) ProSA-web: interactive web service for the recognition of errors in three-dimensional structures of proteins. *Nucleic Acids Res* 35:407-410.

42. Schwieters C D, Kuszewski J J, Tjandra N, Marius Clore G (2003) The Xplor-NIH NMR molecular structure determination package. *J Magn Reson* 160(1):65-73.
43. Hyberts S G, Goldberg M S, Havel T F, Wagner G (1992) The solution structure of eglin c based on measurements of many NOEs and coupling constants and its comparison with X-ray structures. *Protein Sci* 1(6):736-51.
44. Shen Y, Delaglio F, Comilescu G, Bax A (2009) TALOS+: a hybrid method for predicting protein backbone torsion angles from NMR chemical shifts. *J Biomol NMR* 44(4):213-23.
45. Koradi R, Billeter M, Wilthrich K (1996) MOLMOL: a program for display and analysis of macromolecular structures. *J Mol Graph* 14(1):51-5, 29-32.
46. Navon-Venezia S, Feder R, Gaidukov L, Carmeli Y, Mor A (2002) Antibacterial Properties of Dermaseptin S4 Derivatives with In Vivo Activity. *Antimicrob Agents Chemother* 46(3):689-694.
47. Ray A, Dittel B N (2010) Isolation of Mouse Peritoneal Cavity Cells. *J Vis Exp* (35):e1488.
48. Moreno S E, et al. (2006) IL-12, but Not IL-18, Is Critical to Neutrophil Activation and Resistance to Polymicrobial Sepsis Induced by Cecal Ligation and Puncture. *J Immunol* 177(5):3218-3224.
49. Vert M, et al. (2012) Terminology for biorelated polymers and applications (IUPAC Recommendations 2012). *Pure Appl Chem* 84(2):377-410.
50. de la Fuente-Núñez C, Reffuveille F, Fernández L, Hancock R E W (2013) Bacterial biofilm development as a multicellular adaptation: antibiotic resistance and new therapeutic strategies. *Curr Opin Microbiol* 16(5):580-589.
51. Boase N R B, Torres M D T, Fletcher N L, de la Fuente-Nunez C, Fairfull-Smith K E (2018) Polynitroxide copolymers to reduce biofilm fouling on surfaces. *Polym Chem.* doi:10.1039/C8PY01101J.
52. Pizzo E, et al. (2018) Novel bioactive peptides from PD-L1/2, a type 1 ribosome inactivating protein from *Phytolacca dioica* L. Evaluation of their antimicrobial properties and anti-biofilm activities. *Biochim Biophys Acta-Biomembr* 1860(7). doi:10.1016/j.bbamem.2018.04.010.

What is claimed:

1. An antimicrobial peptide that comprises a mastoparan peptide having SEQ ID NO:1 and a pentapeptide motif formed from phenylalanine, leucine, proline, and two isoleucine residues, wherein the pentapeptide motif is conjugated the N-terminus of the mastoparan peptide, wherein the antimicrobial peptide is not SEQ ID NO:5.

2. The antimicrobial peptide according to claim 1 comprising any one of SEQ ID NOS:6-64.

3. The antimicrobial peptide according to claim 1 comprising SEQ ID NO: 19.

4. The antimicrobial peptide according to claim 1 comprising SEQ ID NO: 20.

5. The antimicrobial peptide according to claim 1 comprising SEQ ID NO: 31.

6. The antimicrobial peptide according to claim 1 comprising SEQ ID NO: 38.

7. The antimicrobial peptide according to claim 1 comprising SEQ ID NO: 52.

8. The antimicrobial peptide according to claim 1 comprising SEQ ID NO: 54.

9. The antimicrobial peptide according to claim 1 comprising SEQ ID NO: 59.

10. A method of treating a microbial infection in a subject comprising administering to a subject a therapeutically effective amount of an antimicrobial peptide according to claim 1.

11. A method comprising contacting a biofilm with an effective amount of an antimicrobial peptide according to claim 1.

12. A method of forming an antimicrobial peptide comprising conjugating a pentapeptide motif formed from phenylalanine, leucine, proline, and two isoleucine residues to a mastoparan peptide having SEQ ID NO:1 at the N-terminus of the peptide, wherein the pentapeptide motif is not FLPII.

13. The method according to claim 12 comprising any one of SEQ ID NOS:6-64.

14. The method according to claim 12 comprising SEQ ID NO: 19.

15. The method according to claim 12 comprising SEQ ID NO: 20.

16. The method according to claim 12 comprising SEQ ID NO: 31.

17. The method according to claim 12 comprising SEQ ID NO: 38.

18. The method according to claim 12 comprising SEQ ID NO: 52.

19. The method according to claim 12 comprising SEQ ID NO: 54.

20. The method according to claim 12 comprising SEQ ID NO: 59.

21. A composition comprising an antimicrobial peptide according to claim 1 and a pharmaceutically acceptable carrier.

22. The composition according to claim 21, comprising two or more antimicrobial peptides comprising SEQ ID NOS:5-64.

* * * * *

UNITED STATES PATENT AND TRADEMARK OFFICE
CERTIFICATE OF CORRECTION

PATENT NO. : 12,116,387 B2
APPLICATION NO. : 17/932077
DATED : October 15, 2024
INVENTOR(S) : Marcelo Der Torossian Torres et al.

It is certified that error appears in the above-identified patent and that said Letters Patent is hereby corrected as shown below:

In the Specification

Under Column no. 4, Line no. 35, Replace:
"Four 4 of"
With:
--Four µL of--

Under Column no. 4, Line no. 37, Replace:
"to 1004 of"
With:
--to 100 µL of--

Under Column no. 4, Line no. 40, Replace:
"water (1004 solution"
With:
--water (100 µL solution--

Under Column no. 4, Line no. 48, Replace:
"(0-64 µmoL$^{-1}$) peptides"
With:
--(0-64 µmol L$^{-1}$) peptides--

Under Column no. 14, Line no. 24 (Approx.), Replace:
"(1-400 µmoL$^{-1}$), but"
With:
--(1-400 µmol L$^{-1}$), but--

Signed and Sealed this
Second Day of September, 2025

Coke Morgan Stewart
*Acting Director of the United States Patent and Trademark Office*

Under Column no. 14, Line no. 24 (Approx.), Replace:
"µmoL⁻¹ against"
With:
--µmol L⁻¹ against--

Under Column no. 14, Line no. 27 (Approx.), Replace:
"at 7-50 µmoL⁻¹"
With:
--at 7-50 µmol L⁻¹--

Under Column no. 14, Line no. 38, Replace:
"200 µmoL⁻¹)"
With:
--200 µmol L⁻¹)--

Under Column no. 15, Line no. 60, Replace:
"(FIGS. 4E and"
With:
--(FIG. 4E and--

Under Column no. 18, Line no. 66, Replace:
"tested (128 µmoL⁻¹) (Table 7)"
With:
--tested (128 µmol L⁻¹) (Table 7)--

Under Column no. 19, Line nos. 17-18, Replace:
"Synthetic analogs (IFLPIINLKALAALAKKIL-NH2) (SEQ"
With:
--Synthetic analogs 15 (IFLPIINLKALAALAKKIL-NH₂) (SEQ--

Under Column no. 19, Line no. 19, Replace:
"(FPIILINLKALAALAKKIL-NH2) (SEQ"
With:
--(FPIILINLKALAALAKKIL-NH₂) (SEQ--

Under Column no. 19, Line no. 50, Replace:
"at 70 µmoL⁻¹ and"
With:
--at 70 µmol L⁻¹ and--

Under Column no. 19, Line no. 51, Replace:
"at 50 µmoL⁻¹ were"
With:
--at 50 µmol L⁻¹ were--

CERTIFICATE OF CORRECTION (continued)
U.S. Pat. No. 12,116,387 B2

Under Column no. 20, Line no. 39, Replace:
"(http://mordred.bioc.cam.ac.uk/—rapper/rampage.php)."
With:
--(http://mordred.bioc.cam.ac.uk/~rapper/rampage.php).--

Under Column no. 21, Line no. 8, Replace:
"(http://psys-1_5-dev.nesg.org/). The"
With:
--(http://psvs-1_5-dev.nesg.org/). The--

Under Column no. 21, Line no. 12, Replace:
"(http://mordred.bioc.cam.ac.uk/—rapper/rampage.php)"
With:
--(http://mordred.bioc.cam.ac.uk/~rapper/rampage.php)--

Under Column no. 23, Line no. 12, Replace:
"de Sao Paulo-Ribeirão Preto."
With:
--de São Paulo-Ribeirão Preto.--

Under Column no. 24, Line no. 38, Replace:
"of 20 containing"
With:
--of 20 μL containing--

Under Column no. 25, Line no. 39, Replace:
"ehtj.0.09.001."
With:
--ehtj.09.001.--

Under Column no. 26, Line no. 14 (Approx.), Replace:
"P, Lange Ü,"
With:
--P, Langel Ü,--

Under Column no. 26, Line no. 16 (Approx.), Replace:
"peptide Tpl 0"
With:
--peptide Tp10--

Under Column no. 26, Line no. 36, Replace:
"K, Rahanj am N, Hancock"
With:
--K, Rahanjam N, Hancoc--

Under Column no. 27, Line no. 11 (Approx.), Replace:
"M, Wilthrich K"
With:
--M, Wüthrich K--